(12) United States Patent
Dupont et al.

(10) Patent No.: US 12,114,945 B2
(45) Date of Patent: Oct. 15, 2024

(54) INSTRUMENTS FOR SURGICAL ROBOTIC SYSTEM AND INTERFACES FOR THE SAME

(71) Applicant: Distalmotion SA, Epalinges (CH)

(72) Inventors: Lancelot Dupont, Pully (CH); Julien Chassot, Lechelles (CH)

(73) Assignee: Distalmotion SA, Epalinges (CH)

( * ) Notice: Subject to any disclaimer, the term of this patent is extended or adjusted under 35 U.S.C. 154(b) by 0 days.

(21) Appl. No.: 18/603,045

(22) Filed: Mar. 12, 2024

(65) Prior Publication Data
US 2024/0216087 A1 Jul. 4, 2024

Related U.S. Application Data

(63) Continuation of application No. PCT/IB2022/058437, filed on Sep. 8, 2022.
(Continued)

(51) Int. Cl.
*A61B 34/30* (2016.01)
*A61B 17/00* (2006.01)
(Continued)

(52) U.S. Cl.
CPC ...... *A61B 34/30* (2016.02); *A61B 17/320092* (2013.01); *A61B 34/35* (2016.02);
(Continued)

(58) Field of Classification Search
CPC . A61B 34/30; A61B 34/35; A61B 17/320092; A61B 2034/305; A61B 2017/320093; A61B 2017/00367
See application file for complete search history.

(56) References Cited

U.S. PATENT DOCUMENTS 2,764,301 A 9/1956 Goertz et al.
2,771,199 A 11/1956 Jelatis
(Continued)

FOREIGN PATENT DOCUMENTS

CN 101027010 A 8/2007
CN 101584594 A 11/2009
(Continued)

OTHER PUBLICATIONS

US 9,232,978 B2, 01/2016, Shellenberger (withdrawn)
(Continued)

*Primary Examiner* — Ashley L Fishback
(74) *Attorney, Agent, or Firm* — Cooley LLP

(57) ABSTRACT

Systems and methods for actuating an end-effector of a surgical instrument are provided. The surgical instrument includes a surgical instrument interface operatively coupled to an instrument shaft having an end-effector. The surgical instrument interface includes a pair of actuators slidably disposed within longitudinal openings of a housing of the surgical instrument interface and engaged with a grooved opening of a barrel rotatably disposed within the housing, such that translational movement of the actuators within the longitudinal openings is converted to rotational movement of the barrel along the grooved opening. The surgical instrument interface further may include a torsion spring pre-loaded with a predetermined torque such that rotation of the barrel causes rotation of the instrument shaft if the torque generated between the barrel and the instrument shaft is less than the predetermined torque of the spring. Rotation of the instrument shaft actuates the end-effector via a cam mechanism.

8 Claims, 14 Drawing Sheets

Related U.S. Application Data

(60) Provisional application No. 63/243,527, filed on Sep. 13, 2021.

(51) Int. Cl.
*A61B 17/32* (2006.01)
*A61B 34/35* (2016.01)

(52) U.S. Cl.
CPC ............... *A61B 2017/00367* (2013.01); *A61B 2017/320093* (2017.08); *A61B 2034/305* (2016.02)

(56) References Cited

U.S. PATENT DOCUMENTS

| | | | |
|---|---|---|---|
| 2,774,488 A | 12/1956 | Goertz et al. |
| 2,846,084 A | 8/1958 | Goertz et al. |
| 3,065,863 A | 11/1962 | Saunders, Jr. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker |
| 3,995,209 A | 11/1976 | Weston |
| 4,221,516 A | 9/1980 | Haaker et al. |
| 4,522,196 A | 6/1985 | Cunningham et al. |
| 4,557,164 A | 12/1985 | Krampe |
| 4,756,655 A | 7/1988 | Jameson |
| 4,838,797 A | 6/1989 | Dodier |
| 5,147,357 A | 9/1992 | Rose et al. |
| 5,176,352 A | 1/1993 | Braun |
| 5,207,114 A | 5/1993 | Salisbury, Jr. et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,591,119 A | 1/1997 | Adair |
| 5,599,151 A | 2/1997 | Daum et al. |
| 5,603,723 A | 2/1997 | Aranyi et al. |
| 5,631,973 A | 5/1997 | Green |
| 5,649,955 A | 7/1997 | Hashimoto et al. |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,779,727 A | 7/1998 | Orejola |
| 5,784,542 A | 7/1998 | Ohm et al. |
| 5,792,045 A | 8/1998 | Adair |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,855,583 A | 1/1999 | Wang et al. |
| 5,876,325 A | 3/1999 | Mizuno et al. |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,063,095 A | 5/2000 | Wang et al. |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,375,610 B2 | 4/2002 | Verschuur |
| 6,394,998 B1 | 5/2002 | Wallace et al. |
| 6,435,794 B1 | 8/2002 | Springer |
| 6,436,107 B1 | 8/2002 | Wang et al. |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,799,065 B1 | 9/2004 | Niemeyer |
| 6,817,974 B2 | 11/2004 | Cooper et al. |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,025,064 B2 | 4/2006 | Wang et al. |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,122,032 B2 | 10/2006 | Shinmura et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,331,967 B2 | 2/2008 | Lee et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,886,743 B2 | 2/2011 | Cooper et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,226,546 B2 | 7/2012 | Belson |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,303,576 B2 | 11/2012 | Brock |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |

(56) References Cited

U.S. PATENT DOCUMENTS

| | | |
|---|---|---|
| 8,414,475 B2 | 4/2013 | Sholev |
| 8,418,904 B2 | 4/2013 | Wenchell et al. |
| 8,423,186 B2 | 4/2013 | Itkowitz et al. |
| 8,433,389 B2 | 4/2013 | Geiger et al. |
| 8,435,171 B2 | 5/2013 | Sholev |
| 8,496,152 B2 | 7/2013 | Viola |
| 8,500,132 B2 | 8/2013 | Norton |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,608,773 B2 | 12/2013 | Tierney et al. |
| 8,616,431 B2 | 12/2013 | Timm et al. |
| 8,617,203 B2 | 12/2013 | Stefanchik et al. |
| 8,644,988 B2 | 2/2014 | Prisco et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,753,346 B2 | 6/2014 | Suarez et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,888,688 B2 | 11/2014 | Julian et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,060,795 B2 | 6/2015 | Meenink |
| 9,084,606 B2 | 7/2015 | Greep |
| 9,089,351 B2 | 7/2015 | Park et al. |
| 9,113,860 B2 | 8/2015 | Viola et al. |
| 9,113,861 B2 | 8/2015 | Martin et al. |
| 9,119,657 B2 | 9/2015 | Shelton, IV et al. |
| 9,144,456 B2 | 9/2015 | Rosa et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grünberg et al. |
| 9,314,310 B2 | 4/2016 | Kirschenman et al. |
| 9,333,040 B2 | 5/2016 | Shellenberger et al. |
| 9,345,545 B2 | 5/2016 | Shellenberger et al. |
| 9,358,031 B2 | 6/2016 | Manzo |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grünberg et al. |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,713,509 B2 | 7/2017 | Schuh et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,795,282 B2 | 10/2017 | Sholev et al. |
| 9,795,454 B2 | 10/2017 | Seeber et al. |
| 9,877,794 B2 | 1/2018 | Csiky |
| 9,883,915 B2 | 2/2018 | Rogers et al. |
| 9,884,427 B2 | 2/2018 | Low et al. |
| 9,895,142 B2 | 2/2018 | Sato et al. |
| D816,243 S | 4/2018 | Barber |
| 9,937,013 B2 | 4/2018 | Frimer et al. |
| 9,937,626 B2 | 4/2018 | Rockrohr |
| 9,943,372 B2 | 4/2018 | Sholev et al. |
| 9,943,377 B2 | 4/2018 | Yates et al. |
| 9,980,743 B2 | 5/2018 | Grace et al. |
| 9,993,313 B2 | 6/2018 | Schuh et al. |
| 10,028,792 B2 | 7/2018 | Frimer et al. |
| 10,039,609 B2 | 8/2018 | Frimer et al. |
| 10,039,820 B2 | 8/2018 | Coller et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,179,413 B2 | 1/2019 | Rockrohr |
| 10,201,392 B2 | 2/2019 | Frimer et al. |
| 10,265,129 B2 | 4/2019 | Beira |
| 10,299,873 B2 | 5/2019 | Hares et al. |
| 10,325,072 B2 | 6/2019 | Beira et al. |
| 10,357,320 B2 | 7/2019 | Beira |
| 10,357,324 B2 | 7/2019 | Flatt et al. |
| 10,363,055 B2 | 7/2019 | Beira et al. |
| 10,413,374 B2 | 9/2019 | Chassot et al. |
| 10,433,925 B2 | 10/2019 | Shelton, IV et al. |
| 10,510,447 B2 | 12/2019 | Beira et al. |
| 10,548,680 B2 | 2/2020 | Beira |
| 10,568,709 B2 | 2/2020 | Beira |
| 10,646,294 B2 | 5/2020 | Beira |
| 10,736,705 B2 | 8/2020 | Scheib et al. |
| 10,786,272 B2 | 9/2020 | Beira |
| 10,786,329 B2 | 9/2020 | Schuh et al. |
| 10,792,113 B2 | 10/2020 | Cuthbertson et al. |
| 10,813,713 B2 | 10/2020 | Koch, Jr. et al. |
| 10,864,049 B2 | 12/2020 | Beira |
| 10,864,052 B2 | 12/2020 | Beira |
| 11,039,820 B2 | 6/2021 | Beira |
| 11,058,503 B2 | 7/2021 | Chassot et al. |
| 11,076,922 B2 | 8/2021 | Beira et al. |
| 11,200,980 B2 | 12/2021 | Beira et al. |
| 11,324,619 B1 | 5/2022 | Yacoby et al. |
| 11,337,716 B2 | 5/2022 | Beira |
| 11,426,187 B2 | 8/2022 | Brodbeck et al. |
| 11,478,315 B2 | 10/2022 | Beira |
| 11,510,745 B2 | 11/2022 | Chassot et al. |
| 11,571,195 B2 | 2/2023 | Beira |
| 11,944,337 B2 | 4/2024 | Beira |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll et al. |
| 2003/0013949 A1 | 1/2003 | Moll et al. |
| 2003/0155747 A1 | 8/2003 | Bridges |
| 2003/0208186 A1 | 11/2003 | Moreyra |
| 2003/0216715 A1 | 11/2003 | Moll et al. |
| 2004/0049205 A1 | 3/2004 | Lee et al. |
| 2004/0116906 A1 | 6/2004 | Lipow |
| 2004/0133189 A1 | 7/2004 | Sakurai |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |

(56) References Cited

U.S. PATENT DOCUMENTS

| | | |
|---|---|---|
| 2005/0216045 A1 | 9/2005 | Young et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 | 11/2008 | Abou El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0192522 A1 | 7/2009 | Blumenkranz |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2009/0326322 A1 | 12/2009 | Diolaiti |
| 2009/0326552 A1 | 12/2009 | Diolaiti |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0234857 A1 | 9/2010 | Itkowitz et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0082462 A1 | 4/2011 | Suarez et al. |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0282491 A1 | 11/2011 | Prisco et al. |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0245643 A1 | 9/2013 | Woodard, Jr. et al. |
| 2013/0245647 A1 | 9/2013 | Martin et al. |
| 2013/0282027 A1 | 10/2013 | Woodard, Jr. et al. |
| 2013/0303408 A1 | 11/2013 | Indermuhle |
| 2013/0304070 A1 | 11/2013 | Nelson et al. |
| 2013/0304083 A1 | 11/2013 | Kaercher et al. |
| 2013/0304084 A1 | 11/2013 | Beira et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0039527 A1 | 2/2014 | Avelar et al. |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0135794 A1 | 5/2014 | Cau |
| 2014/0142595 A1 | 5/2014 | Awtar et al. |
| 2014/0166023 A1 | 6/2014 | Kishi |
| 2014/0180308 A1 | 6/2014 | Von Grünberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0277203 A1 | 9/2014 | Atoulikian et al. |
| 2014/0340796 A1 | 11/2014 | Sandhu et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0173840 A1 | 6/2015 | Lohmeier |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0302876 A1 | 10/2016 | Teichtmann |
| 2016/0303743 A1 | 10/2016 | Rockrohr |
| 2016/0346053 A1 | 12/2016 | Beira |
| 2016/0374766 A1 | 12/2016 | Schuh |
| 2017/0020615 A1 | 1/2017 | Koenig et al. |
| 2017/0065364 A1 | 3/2017 | Schuh et al. |
| 2017/0196599 A1 | 7/2017 | Kwon et al. |
| 2017/0215976 A1 | 8/2017 | Nowlin et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |

(56) References Cited

U.S. PATENT DOCUMENTS

| | | | |
|---|---|---|---|
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0168760 A1 | 6/2018 | Koch, Jr. et al. |
| 2018/0214223 A1 | 8/2018 | Turner |
| 2018/0242991 A1 | 8/2018 | Beira |
| 2018/0353251 A1 | 12/2018 | Cuthbertson et al. |
| 2018/0353252 A1 | 12/2018 | Chassot et al. |
| 2018/0360548 A1 | 12/2018 | Marshall et al. |
| 2019/0133698 A1 | 5/2019 | Beira et al. |
| 2019/0239968 A1 | 8/2019 | Beira |
| 2019/0328473 A1 | 10/2019 | Chassot et al. |
| 2020/0105412 A1 | 4/2020 | Beira et al. |
| 2020/0268464 A1 | 8/2020 | Beira |
| 2021/0106348 A1 | 4/2021 | Beira |
| 2021/0330407 A1 | 10/2021 | Chassot et al. |
| 2021/0330408 A1 | 10/2021 | Chassot et al. |
| 2021/0369360 A1 | 12/2021 | Beira et al. |
| 2022/0280179 A1 | 9/2022 | Beira |
| 2023/0054176 A1 | 2/2023 | Beira |
| 2023/0082915 A1 | 3/2023 | Chassot et al. |
| 2023/0125213 A1 | 4/2023 | Chassot et al. |
| 2023/0149002 A1 | 5/2023 | Beira |
| 2024/0033026 A1 | 2/2024 | Chassot et al. |

FOREIGN PATENT DOCUMENTS

| | | | |
|---|---|---|---|
| CN | 101637402 A | 2/2010 |
| CN | 101732093 A | 6/2010 |
| CN | 103717355 A | 4/2014 |
| DE | 4303311 A1 | 8/1994 |
| DE | 19652792 C2 | 5/1999 |
| DE | 10314827 B3 | 4/2004 |
| DE | 10314828 B3 | 7/2004 |
| DE | 102012008537 A1 | 10/2013 |
| DE | 102012222755 A1 | 6/2014 |
| DE | 102014205036 A1 | 9/2015 |
| DE | 102014205159 A1 | 9/2015 |
| EP | 0595291 A1 | 5/1994 |
| EP | 0621009 A1 | 10/1994 |
| EP | 0677275 A2 | 10/1995 |
| EP | 0776739 A2 | 6/1997 |
| EP | 1254642 A1 | 11/2002 |
| EP | 1279371 B1 | 12/2004 |
| EP | 1886630 A2 | 2/2008 |
| EP | 1889579 A2 | 2/2008 |
| EP | 1889583 A1 | 2/2008 |
| EP | 2058090 A2 | 5/2009 |
| EP | 1977677 B1 | 8/2009 |
| EP | 2095778 A1 | 9/2009 |
| EP | 1889583 B1 | 4/2011 |
| EP | 2377477 B1 | 5/2012 |
| EP | 2473119 A2 | 7/2012 |
| EP | 2305144 B1 | 10/2012 |
| EP | 2044893 B1 | 7/2013 |
| EP | 2653110 A1 | 10/2013 |
| EP | 2679192 A2 | 1/2014 |
| EP | 2736680 A2 | 6/2014 |
| EP | 2777561 A1 | 9/2014 |
| EP | 2783643 A1 | 10/2014 |
| EP | 2837340 A1 | 2/2015 |
| EP | 2837354 A1 | 2/2015 |
| EP | 2554131 B1 | 8/2015 |
| EP | 2777561 B1 | 10/2015 |
| EP | 2979657 A1 | 2/2016 |
| EP | 2837340 B1 | 10/2016 |
| EP | 3111879 A1 | 1/2017 |
| EP | 2783643 B1 | 1/2019 |
| EP | 3613377 A1 | 2/2020 |
| GB | 834244 A | 5/1960 |
| GB | 969899 A | 9/1964 |
| JP | 2004041580 A | 2/2004 |
| JP | 3653856 B2 | 6/2005 |
| JP | 2007290096 A | 11/2007 |
| JP | 2008104620 A | 5/2008 |
| JP | 2009018027 A | 1/2009 |
| KR | 20110032444 A | 3/2011 |
| KR | 20130031403 A | 3/2013 |
| SU | 722754 A1 | 3/1980 |
| WO | WO-8200611 A1 | 3/1982 |
| WO | WO-9743942 A1 | 11/1997 |
| WO | WO-9825666 A1 | 6/1998 |
| WO | WO-0197717 A1 | 12/2001 |
| WO | WO-03067341 A2 | 8/2003 |
| WO | WO-03086219 A2 | 10/2003 |
| WO | WO-2004052171 A2 | 6/2004 |
| WO | WO-2005009482 A2 | 2/2005 |
| WO | WO-2005046500 A1 | 5/2005 |
| WO | WO-2006086663 A2 | 8/2006 |
| WO | WO-2007133065 A1 | 11/2007 |
| WO | WO-2007146987 A2 | 12/2007 |
| WO | WO-2008070556 A1 | 6/2008 |
| WO | WO-2008130235 A2 | 10/2008 |
| WO | WO-2009091497 A2 | 7/2009 |
| WO | WO-2009095893 A2 | 8/2009 |
| WO | WO-2009145572 A2 | 12/2009 |
| WO | WO-2009157719 A2 | 12/2009 |
| WO | WO-2010019001 A2 | 2/2010 |
| WO | WO-2010030114 A2 | 3/2010 |
| WO | WO-2010050771 A2 | 5/2010 |
| WO | WO-2010083480 A2 | 7/2010 |
| WO | WO-2010096580 A1 | 8/2010 |
| WO | WO-2010130817 A1 | 11/2010 |
| WO | WO-2011025818 A1 | 3/2011 |
| WO | WO-2011027183 A2 | 3/2011 |
| WO | WO-2011108840 A2 | 9/2011 |
| WO | WO-2011123669 A1 | 10/2011 |
| WO | WO-2011161626 A2 | 12/2011 |
| WO | WO-2012020386 A1 | 2/2012 |
| WO | WO-2012049623 A1 | 4/2012 |
| WO | WO-2013007784 A1 | 1/2013 |
| WO | WO-2013014621 A2 | 1/2013 |
| WO | WO-2014012780 A1 | 1/2014 |
| WO | WO-2014018447 A1 | 1/2014 |
| WO | WO-2014067804 A1 | 5/2014 |
| WO | WO-2014094716 A1 | 6/2014 |
| WO | WO-2014094717 A1 | 6/2014 |
| WO | WO-2014094718 A1 | 6/2014 |
| WO | WO-2014094719 A1 | 6/2014 |
| WO | WO-2014139023 A1 | 9/2014 |
| WO | WO-2014145148 A2 | 9/2014 |
| WO | WO-2014156221 A1 | 10/2014 |
| WO | WO-2014201010 A1 | 12/2014 |
| WO | WO-2014201538 A1 | 12/2014 |
| WO | WO-2015081946 A1 | 6/2015 |
| WO | WO-2015081947 A1 | 6/2015 |
| WO | WO-2015088647 A1 | 6/2015 |
| WO | WO-2015088655 A1 | 6/2015 |
| WO | WO-2015111475 A1 | 7/2015 |
| WO | WO-2015113933 A1 | 8/2015 |
| WO | WO-2015129383 A1 | 9/2015 |
| WO | WO-2015139674 A1 | 9/2015 |
| WO | WO-2015175200 A1 | 11/2015 |
| WO | WO-2016030767 A1 | 3/2016 |
| WO | WO-2016083189 A1 | 6/2016 |
| WO | WO-2016097861 A1 | 6/2016 |
| WO | WO-2016097864 A2 | 6/2016 |
| WO | WO-2016097868 A1 | 6/2016 |
| WO | WO-2016097871 A1 | 6/2016 |
| WO | WO-2016097873 A2 | 6/2016 |
| WO | WO-2016154173 A1 | 9/2016 |
| WO | WO-2016162751 A1 | 10/2016 |
| WO | WO-2016162752 A1 | 10/2016 |
| WO | WO-2016183054 A1 | 11/2016 |
| WO | WO-2016189284 A1 | 12/2016 |
| WO | WO-2016209891 A1 | 12/2016 |
| WO | WO-2017015599 A1 | 1/2017 |
| WO | WO-2017037532 A1 | 3/2017 |
| WO | WO-2017064301 A1 | 4/2017 |
| WO | WO-2017064303 A1 | 4/2017 |

(56) References Cited

FOREIGN PATENT DOCUMENTS

| | | |
|---|---|---|
| WO | WO-2017064305 A1 | 4/2017 |
| WO | WO-2017064306 A1 | 4/2017 |
| WO | WO-2017134077 A1 | 8/2017 |
| WO | WO-2017220978 A1 | 12/2017 |
| WO | WO-2018142112 A1 | 8/2018 |
| WO | WO-2018162921 A1 | 9/2018 |
| WO | WO-2018207136 A1 | 11/2018 |
| WO | WO-2019099346 A2 | 5/2019 |
| WO | WO-2020131304 A1 | 6/2020 |
| WO | WO-2020141487 A2 | 7/2020 |
| WO | WO-2020237400 A1 | 12/2020 |
| WO | WO-2020263870 A1 | 12/2020 |
| WO | WO-2023037273 A1 | 3/2023 |
| WO | WO-2023073565 A1 | 5/2023 |
| WO | WO-2024084422 A1 | 4/2024 |

OTHER PUBLICATIONS

Abbott et al., Design of an Endoluminal Notes Robotic System, IEEE/RSJ International Conference on Intelligent Robots and Systems, 2007, San Diego, CA (pp. 410-416).

Aesculap Surgical Technologies, Aesculap.RTM. Caiman™, Advanced Bipolar Seal and Cut Technology Brochure, 6 pages (retrieved Aug. 31, 2015).

Arata, et al., Development of a dexterous minimally-invasive surgical system with augmented force feedback capability, IEEE/RSJ International Conference on Intelligent Robots and Systems, 2005 (pp. 3207-3212).

Cavusoglu, et al., Laparoscopic Telesurgical Workstation, IEEE Transactions on Robotics and Automation, (15)4:728-739 (1999).

Charles, et al., Dexterity-enhanced Telerobotic Microsurgery, 8th International Conference Advanced Robotics, pp. 5-10 (1997).

Dachs, et al., Novel Surgical Robot Design: Minimizing the Operating Envelope Within the Sterile Field, 28th International Conference, IEEE Engineering in Medicine Biology Society, 2006, New York (pp. 1505-1508).

Dario, et al., "Novel Mechatronic Tool for Computer-Assisted Arthroscopy," IEEE Transactions on Information Technology in Biomedicine, 4(1):15-29 (Mar. 2000).

Focacci, et al., Lightweight Hand-held Robot for Laparoscopic Surgery, IEEE International Conference on Robotics & Automation, Rome, Italy, pp. 599-604 (2007).

Guthart, et al., The Intuitive™. Telesurgery System: Overview and Application, IEEE International Conference on Robotics & Automation, San Francisco, CA, 2000 (pp. 618-621 ).

Ikuta, et al., Development of Remote Microsurgery Robot and New Surgical Procedure for Deep and Narrow Space, IEEE International Conference on Robotics & Automation, Taipei, Taiwan, 2003 (pp. 1103-1108).

Ikuta, et al., Hyper Redundant Miniature Manipulator 'Hyper Finger' for Remote Minimally Invasive Surgery in Deep Area, IEEE International Conference on Robotics & Automation, Taipei, Taiwan, 2003 (pp. 1098-1102).

Ishii, et al., Development of a New Bending Mechanism and Its Application to Robotic Forceps Manipulator, IEEE International Conference on Robotics & Automation, Rome, Italy, 2007 (pp. 238-243).

Kobayashi, et al., Small Occupancy Robotic Mechanisms for Endoscopic Surgery, International Conference on Medical Image Computing and Computer Assisted Interventions, 2002, (pp. 75-82).

Lang, et al., Intra-operative robotics: NeuroArm., Acta Neurochir. Suppl, 109:231-236 (2011).

Mayer, et al., The Endo [PA]R System for Minimally Invasive Robotic Surgery, IEEE/RSJ International Conference on Intelligent Robots and Systems, Sendai, Japan, 2004 (pp. 3637-3642).

Mitsuishi, et al., Development of a Remote Minimally Invasive Surgical System with Operational Environment Transmission Capability, IEEE International Conference on Robotics & Automation, Taipei, Taiwan, 2003, (pp. 2663-2670).

Mitsuishi, et al., Master-Slave Robotic Platform and its Feasibility Study for Micro-Neurosurgery, Int. J. Med. Robot., 9(2):180-9 (2013).

Morita, et al., Microsurgical Robotic System for the Deep Surgical Field: Development of a Prototype and Feasibility Studies in Animal and Cadaveric Models, J. Neurosurg., 103(2):320-7 (2005).

Nakamura, et al., Multi-DOF Forceps Manipulator System for Laparoscopic Surgery-Mechanism Miniaturized & Evaluation of New Interface, 4th International Conference on Medical Image Computing and Computer assisted Interventions (MICCAI2001 ), 2001 (pp. 606-613).

Peirs, et al., "Design of an Advanced Tool Guiding System for Robotic Surgery," IEEE International Conference on Robotics & Automation, Taipei, Taiwan, 2003, (pp. 2651-2656).

Salle, et al., Optimal Design of High Dexterity Modular MIS Instrument for Coronary Artery Bypass Grafting, IEEE International Conference on Robotics & Automation, New Orleans, LA, 2004, (pp. 1276-1281 ).

Seibold, et al., Prototype of Instrument for Minimally Invasive Surgery with 6-Axis Force Sensing Capability, IEEE International Conference on Robotics & Automation, Barcelona, Spain, 2005, (pp. 496-501 ).

Simaan, et al., Dexterous System for Laryngeal Surgery: Multi-Backbone Bending Snake-like Slaves for Teleoperated Dexterous Surgical Tool Manipulation, IEEE International Conference on Robotics & Automation, New Orleans, LA, 2004 (pp. 351-357).

Stryker™, Endoscopy, Take a Look Around, Ideal Eyes.TM. FFD122 HD, Articulating Laparoscope Brochure, 2 pages (2009).

Tavakoli, et al., Force Reflective Master-Slave System for Minimally Invasive Surgery, IEEE/RSJ International Conference on Intelligent Robots and Systems, Las Vegas, NV, 2003, (pp. 3077-3082).

Taylor, et al., Steady-Hand Robotic System for Microsurgical Augmentation, The International Journal of Robotics Research, 18(12):1201-1210 (1999).

www.cttc.co/technologies/maestro-non-robotic-dexterous-laproscopic-instrum-ent-writsproviding- seven-degrees, Maestro: Non-Robotic Dexterous Laproscopic Instrument With a Wrist Providing Seven Degrees of Freedom, accessed Nov. 12, 2015, 4 pages.

Yamashita, et al., Development of Endoscopic Forceps Manipulator Using Multi-Slider Linkage Mechanisms, The 1st Asian Symposium on Computer Aided Surgery-Robotic and Image-Guided Surgery, Ibaraki, Japan, 4 pages (2005).

Zeus, Robotic Surgical System, available at http://allaboutroboticsurgery.com/zeusrobot.html. (2017) 4 pages.

International Search Report and Written Opinion mailed on Dec. 15, 2022, for PCT Application No. PCT/IB2022/058437, filed on Sep. 8, 2022, 13 pages.

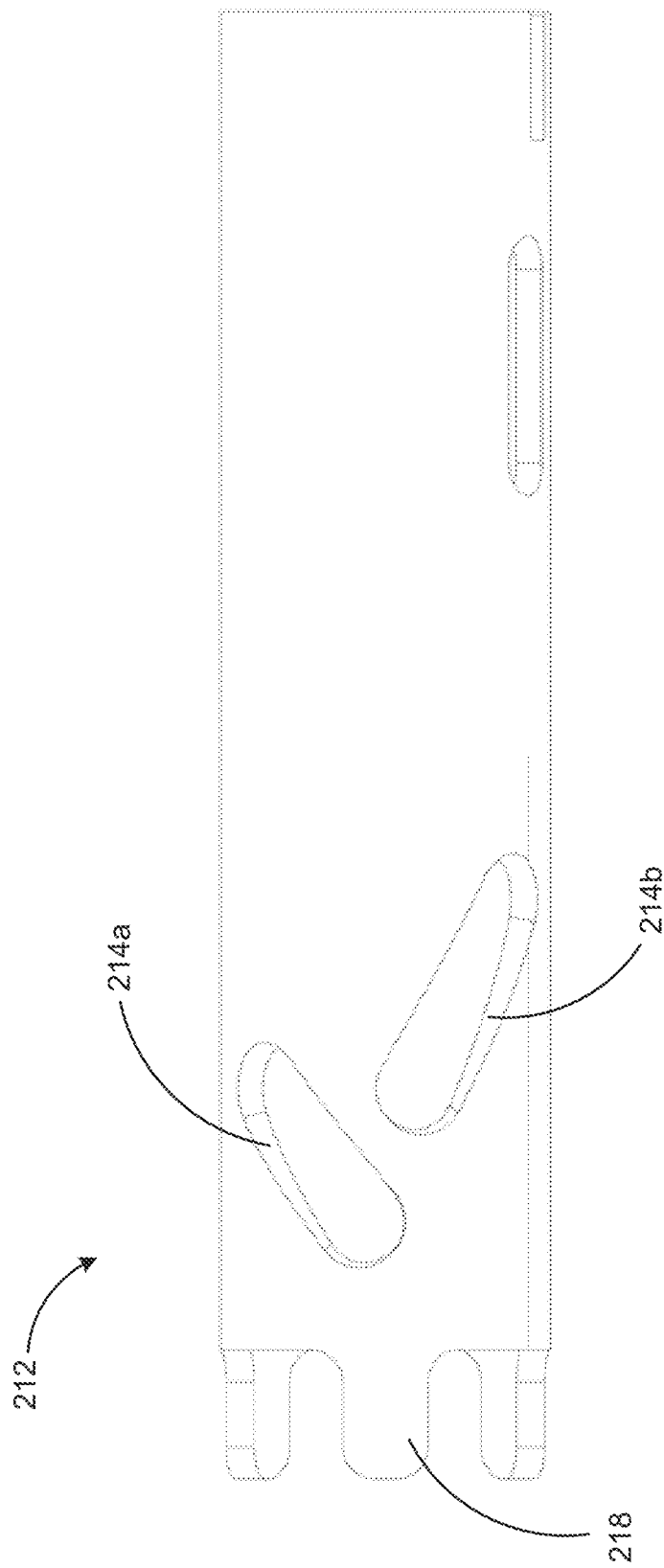

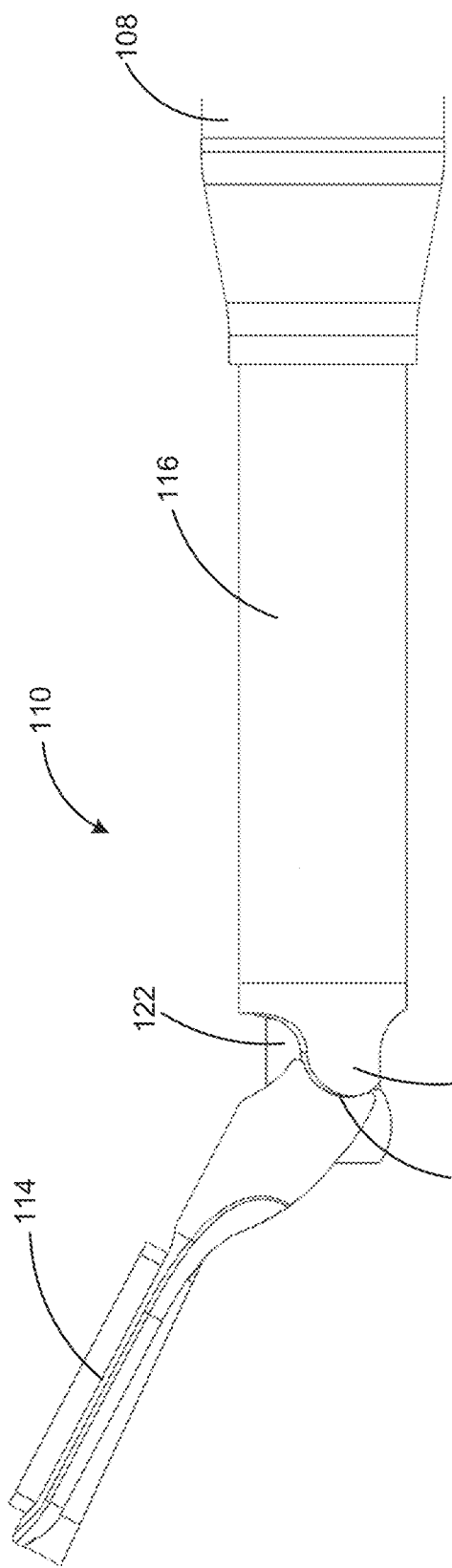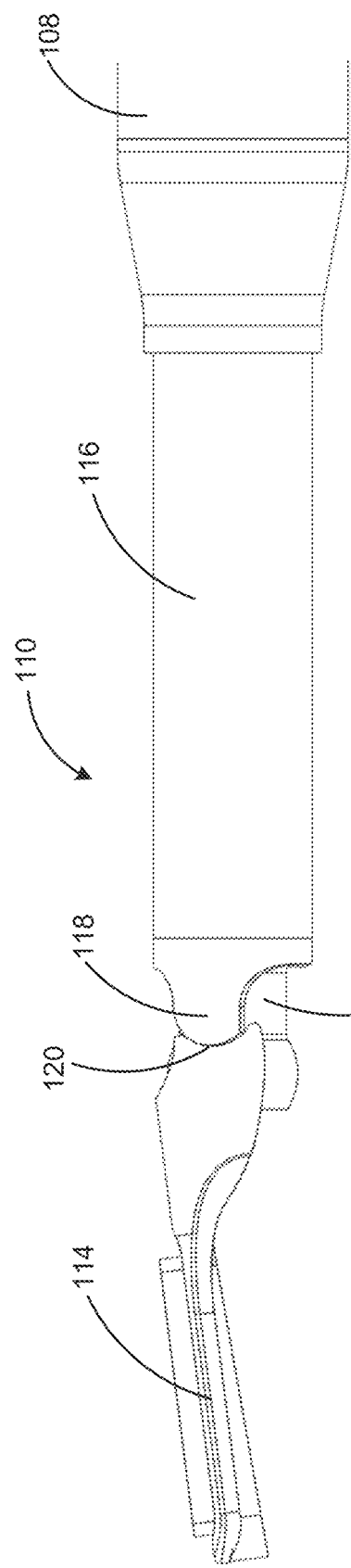
FIG. 11A
FIG. 11B

INSTRUMENTS FOR SURGICAL ROBOTIC SYSTEM AND INTERFACES FOR THE SAME

FIELD OF USE

This application is a continuation of International Application No. PCT/IB2022/058437, filed Sep. 8, 2022, which claims priority to U.S. Provisional Patent Application Ser. No. 63/243,527, filed Sep. 13, 2021, the entire contents of which are incorporated herein by reference.

The present disclosure is directed to surgical instruments and interfaces for the same such as, for example, removable surgical instruments for remotely actuated surgical robot systems.

BACKGROUND

Numerous environments and applications call for remote actuation with teleoperated surgical devices. These applications include the ability to perform fine manipulation, to manipulate in confined spaces, manipulate in dangerous or contaminated environments, in clean-room or sterile environments and in surgical environments, whether open field or minimally invasive. While these applications vary, along with parameters such as precise tolerances and the level of skill of the end user, each demands many of the same features from a teleoperated system, such as the ability to carry out dexterous manipulation with high precision.

Surgical applications are discussed in the following disclosure in more detail as exemplary of applications for a teleoperated device system where known devices exist but significant shortcomings are evident in previously-known systems and methods.

Open surgery is still the preferred method for many surgical procedures. It has been used by the medical community for many decades and typically required making long incisions in the abdomen or other area of the body, through which traditional surgical tools are inserted. Due to such incisions, this extremely invasive approach results in substantial blood loss during surgery and, typically, long and painful recuperation periods in a hospital setting.

Laparoscopy, a minimally invasive technique, was developed to overcome some of the disadvantages of open surgery. Instead of large through-wall incisions, several small openings are made in the patient through which long and thin surgical instruments and endoscopic cameras are inserted. The minimally invasive nature of laparoscopic procedures reduces blood loss and pain and shortens hospital stays. When performed by experienced surgeons, a laparoscopic technique can attain clinical outcomes similar to open surgery. However, despite the above-mentioned advantages, laparoscopy requires a high degree of skill to successfully manipulate the rigid and long instrumentation used in such procedures. Typically, the entry incision acts as a point of rotation, decreasing the freedom for positioning and orientating the instruments inside the patient. The movements of the surgeon's hand about this incision point are inverted and scaled-up relative to the instrument tip ("fulcrum effect"), which reduces dexterity and sensitivity and magnifies any tremors of the surgeon's hands. In addition, the long and straight instruments force the surgeon to work in an uncomfortable posture for hands, arms and body, which can be tremendously tiring during a prolonged procedure. Therefore, due to these drawbacks of laparoscopic instrumentation, minimally invasive techniques are mainly limited to use in simple surgeries, while only a small minority of surgeons is able to use such instrumentation and methods in complex procedures.

To overcome the foregoing limitations of previously-known systems, surgical robotic systems were developed to provide an easier-to-use approach to complex minimally invasive surgeries. By means of a computerized robotic interface, those systems enable the performance of remote laparoscopy where the surgeon sits at a console manipulating two master manipulators to perform the operation through several small incisions. Like laparoscopy, the robotic approach is also minimally invasive, providing the above-mentioned advantages over open surgery with respect to reduced pain, blood loss, and recuperation time. In addition, it also offers better ergonomy for the surgeon compared to open and laparoscopic techniques, improved dexterity, precision, and tremor suppression, and the removal of the fulcrum effect. Although being technically easier, robotic surgery still involves several drawbacks. One major disadvantage of previously-known robotic surgical systems relates to the extremely high complexity of such systems, which contain four to five robotic arms to replace the hands of both the surgeon and the assistant, integrated endoscopic imaging systems, as well as the ability to perform remote surgery, leading to huge capital costs for acquisition and maintenance, and limiting the affordably for the majority of surgical departments worldwide. Another drawback of these systems is the bulkiness of previously-known surgical robots, which compete for precious space within the operating room environment and significantly increasing preparation time. Access to the patient thus may be impaired, which raises safety concerns.

For example, the da Vinci® surgical systems (available by Intuitive Surgical, Inc., Sunnyvale, California, USA) is a robotic surgical system for allowing performance of remote laparoscopy by a surgeon. However, the da Vinci® surgical systems are very complex robotic systems, with each system costing around $2,000,000 per robot, $150,000 per year for servicing, and $2,000 per surgery for surgical instruments. The da Vinci® surgical system also requires a lot of space in the operating room, making it hard to move around to a desired location within the operating room, and difficult to switch between forward and reverse surgical workspaces (also known as multi-quadrant surgery).

Moreover, as the surgeon's operating console is typically positioned away from the surgical site, the surgeon and the operating console are not in the sterile zone of the operating room. If the surgeon's operating console is not sterile, the surgeon is not permitted to attend to the patient if necessary without undergoing additional sterilization procedures. During certain surgical operations, a surgeon may need to intervene at a moment's notice, and current bulky robotic systems may prevent the surgeon from quickly accessing the surgical site on the patient in a timely, life-saving manner.

WO97/43942 to Madhani, WO98/25666 to Cooper, and U.S. Patent Application Publication No. 2010/0011900 to Burbank each discloses a robotic teleoperated surgical instrument designed to replicate a surgeon's hand movements inside the patient's body. By means of a computerized, robotic interface, the instrument enables the performance of remote laparoscopy, in which the surgeon, seated at a console and manipulating two joysticks, performs the operation through several small incisions. Those systems do not have autonomy or artificial intelligence, being essentially a sophisticated tool that is fully controlled by the surgeon. The control commands are transmitted between the robotic master and robotic slave by a complex computer-controlled mechatronic system, which is extremely costly to produce and maintain and requires considerable training for the hospital staff.

WO2013/014621 to Beira, the entire contents of which are incorporated herein by reference, describes a mechanical teleoperated device for remote manipulation which comprises master-slave configuration including a slave unit driven by a kinematically equivalent master unit, such that each part of the slave unit mimics the movement of a corresponding part of the master unit. A typical master-slave telemanipulator provides movement in seven degrees-of-freedom. Specifically, these degrees of freedom include three translational macro movements, e.g., inward/outward, upward/downward, and left/right degrees-of-freedoms, and four micro movements including one rotational degree-of-freedom, e.g., roll, two articulation degrees-of-freedom, e.g., yaw and pitch, and one actuation degree-of-freedom, e.g., open/close. Although the mechanical transmission system described in that publication is well adapted to the device, the low-friction routing of the cables from handles through the entire kinematic chain to the instruments is costly, complex, bulky, and requires precise calibration and careful handling and maintenance.

In addition, previously-known purely mechanical solutions do not offer wrist alignment, low device complexity, low mass and inertia, high surgical volume, and good haptic feedback. For example, with a purely mechanical teleoperated device, in order to perform a pure pronosupination/roll movement of the instrument, the surgeon typically has to perform a combined pronosupination/roll movement of his hand/forearm as well as a translational movement on a curved path with his wrist. Such movements are complex to execute properly, and if not done properly, the end-effector pitches and yaws creating undesired parasitic movements.

Further, the routing of the articulation and actuation degrees-of-freedom cables through mechanical telemanipulators may limit the dexterity of the angular range of the various joints of the telemanipulator link-and-joint structure. This in turn limits the available surgical volume of the instruments accessible within the patient. During rapid movements of the mechanical telemanipulators, inertia of the telemanipulators also may be disturbing and result in over-shoot of the target and fatigue of the surgeon's hand. Part of this mass can be attributed to parts and components required to route the actuation and articulation degrees-of-freedom.

Accordingly, it would be desirable to provide remotely actuated surgical robot systems having robotic telemanipulators that are well adapted for use by the surgeon, seamlessly integrated into the operation room, allow for a surgeon to work between the robot and the patient in a sterile manner, are relatively low cost, and/or permit integrated laparoscopy.

It would further be desirable to provide a remotely actuated surgical robot having mechanical and/or electro-mechanical telemanipulators.

Moreover, it is desirable to provide advanced energy instrumentation on a robotic system, such as ultrasonic dissectors. Accordingly, there is a need for surgical instrumentation having a rigid and plain sonotrode coaxial with the instrument shaft, which does not allow for the use of traditional cable driven transmission. Thus, it would further be desirable to provide surgical instruments having a surgical instrument interface that does not require cables to actuate the end-effector of the surgical instrument. In addition, as it is desirable for the closing force of such instruments to be precisely controlled, there is a need for such surgical instruments to have reduced torque.

SUMMARY

The present invention overcomes the drawbacks of previously-known systems by providing surgical instruments having a surgical instrument interface for interchangeably coupling with a patient hub of a patient console of a robotic telemanipulator system and/or for a handheld surgical system, and for actuating an end-effector of the surgical instrument without cable transmission.

As will be understood by a person having ordinary skill in the art, the term "master" used herein refers to components controlled by the surgeon and may be referred to as "surgeon," and the term "slave" used herein refers to components that interact with the patient undergoing the surgery and may be referred to as "patient." For example, the terms "master console" and "surgeon console" are interchangeable and the terms "slave console" and "patient console" are interchangeable, etc.

In accordance with one aspect of the present disclosure, a surgical instrument interface operatively coupled to an instrument shaft having an end-effector is provided. The surgical instrument interface includes a housing having a longitudinal opening, and a barrel rotatably disposed within the housing. The barrel includes a grooved opening extending circumferentially along at least a portion of the barrel. Moreover, the surgical instrument interface further includes an actuator slidably disposed within the longitudinal opening and engaged with the grooved opening, such that translational movement of the actuator along the longitudinal opening causes the barrel to rotate along the grooved opening to thereby rotate the instrument shaft. In some embodiments, the surgical instrument interface may include a spring having a proximal end coupled to the barrel and a distal end coupled to the instrument shaft. The spring may be pre-loaded with a predetermined torque. Accordingly, translational movement of the actuator along the longitudinal opening may cause the barrel to rotate along the grooved opening to thereby rotate the instrument shaft via the spring.

For example, rotation of the barrel causes the instrument shaft to rotate when a torque generated by rotation of the barrel between the barrel and the instrument shaft is less than the predetermined torque of the spring. In addition, when the torque generated by rotation of the barrel between the barrel and the instrument shaft is less than the predetermined torque of the spring, the spring transmits the torque to the instrument shaft to rotate the instrument shaft in a first direction.

In some embodiments, the barrel includes a cam stop that engages with a cam ring fixed to the instrument shaft. Thus, when the torque generated by rotation of the barrel between the barrel and the instrument shaft is less than the predetermined torque of the spring, the cam stop transmits the torque to the instrument shaft via the cam ring to rotate the instrument shaft in a second direction opposite to the first direction. For example, the barrel stop extends proximally from a proximal end of the barrel, and the cam ring has a distal opening sized and shaped to receive the cam stop and to permit the cam stop to circumferentially move within the distal opening.

Moreover, when a torque generated by rotation of the barrel between the barrel and the instrument shaft is greater than the predetermined torque of the spring, rotation of the barrel in a first direction causes the spring to compress torsionally such that rotation torque of the barrel in the first direction limits the torque transmitted to the shaft to the torsion torque of the spring. Additionally, rotation of the barrel in a second direction opposite to the first direction causes the spring to absorb movement of the barrel until the barrel is able to transmit torque to the instrument shaft. In some embodiments, the distal end of the spring is coupled to the instrument shaft via a fixation ring, which may be actuated to pre-load the spring with the predetermined torque.

The housing may include a second longitudinal opening, such that the surgical instrument interface further includes a second actuator slidably disposed within the second longitudinal opening and engaged with the grooved opening. Accordingly, translational movement of the second actuator along the second longitudinal opening causes the barrel to rotate along the grooved opening to thereby rotate the instrument shaft, e.g., via the spring. The grooved opening may have a shape that permits the first and second actuators to move in opposite directions along the respective longitudinal openings to thereby rotate the barrel. In some embodiments, the grooved opening includes first and second grooved openings, each of the first and second grooved openings sized and shaped to be engaged with a corresponding actuator. In some embodiments, the end-effector may emit ultrasonic energy. Moreover, the end-effector may include a pair of jaws. Accordingly, rotation of the instrument shaft may cause a first jaw of the pair of jaws to move relative to a second jaw of the pair of jaws of the end-effector to thereby cause the end-effector to open and close. Preferably, the first jaw is operatively coupled to the instrument shaft via a cam mechanism such that rotation of the instrument shaft causes the end-effector to open and close.

In accordance with another aspect of the present disclosure, a surgical instrument that may be attached to a surgical platform is provided. The surgical instrument includes the surgical instrument interface described above, an instrument shaft operatively coupled to the surgical instrument interface, and an end-effector disposed at a distal end of the instrument shaft.

In accordance with yet another aspect of the present disclosure, a surgical robot system that may be releasably coupled to the surgical instrument described above is provided. The surgical robot system may be a surgical platform having a patient console, which may releasably engage with the actuator of the surgical instrument interface.

In accordance with another aspect of the present disclosure, a method for actuating an end-effector of a surgical instrument is provided. The method includes selecting a surgical instrument interface operatively coupled to an instrument shaft having the end-effector, the surgical instrument interface including a housing having a longitudinal opening, a barrel rotatably disposed within the housing; and translationally moving an actuator disposed within the longitudinal opening and engaged with a grooved opening extending circumferentially along at least a portion of the barrel, to thereby cause the barrel to rotate along the grooved opening which causes rotation of the instrument shaft. In some embodiments, the method includes selecting a surgical instrument interface further having a spring coupled to the barrel and the instrument shaft, such that the spring may be pre-loaded with a predetermined torque. Accordingly, translationally moving the actuator causes the barrel to rotate along the grooved opening which causes rotation of the instrument shaft via the spring when a torque generated by rotation of the barrel between the barrel and the instrument shaft is less than the predetermined torque of the spring. When the torque generated by rotation of the barrel between the barrel and the instrument shaft is greater than the predetermined torque of the spring, rotation of the barrel causes the spring to compress torsionally, such that rotation torque of the barrel limits the torque transmitted to the shaft to the torsion torque of the spring.

The method further includes translationally moving a second actuator disposed within a second longitudinal opening of the housing and engaged with a second grooved opening extending circumferentially along at least a portion of the barrel, to thereby cause the barrel to rotate along the second grooved opening which causes rotation of the instrument shaft, e.g., via the spring when the torque generated by rotation of the barrel between the barrel and the instrument shaft is less than the predetermined torque of the spring. The actuators translationally move in opposite directions. Accordingly, rotation of the instrument shaft may cause a first jaw of the end-effector to move relative to a second jaw of the end-effector via a cam mechanism to thereby cause the end-effector to open and close. The method further may include emitting ultrasonic energy via the end-effector.

BRIEF DESCRIPTION OF THE DRAWINGS

FIG. 5 illustrates an exemplary rotation barrel of the surgical instrument of FIGS. 4A and 4B constructed in accordance with the principles of the present disclosure.

FIGS. 11A and 11B illustrate actuation of the end-effector of FIGS. 10A and 10B in accordance with the principles of the present disclosure.

DETAILED DESCRIPTION

A surgical instrument having a surgical instrument interface is described herein. The surgical instrument interface may be used for interchangeably coupling with a patient hub of a patient console of a robotic telemanipulator system and/or with a handheld surgical system, and for actuating an end-effector of the surgical instrument without cable transmission. The surgical instrument interface permits actuation of the end-effector of the surgical instrument by translating translational movement of one or more actuators of the surgical instrument interface into rotational movement of an instrument shaft of the surgical instrument. The rotational movement of the instrument may then be translated to actuation of the end-effector in a degree-of-freedom, e.g., open and close, via, for example, a cam mechanism between the instrument shaft and the end-effector, as described in U.S. 2005/0216045 to Young, the entire contents of which are incorporated herein by reference. Accordingly, this configuration does not require cable transmission to actuate the end-effector. In addition, the end-effector may be actuated to emit ultrasonic energy for various surgical procedures.

Figure 1:
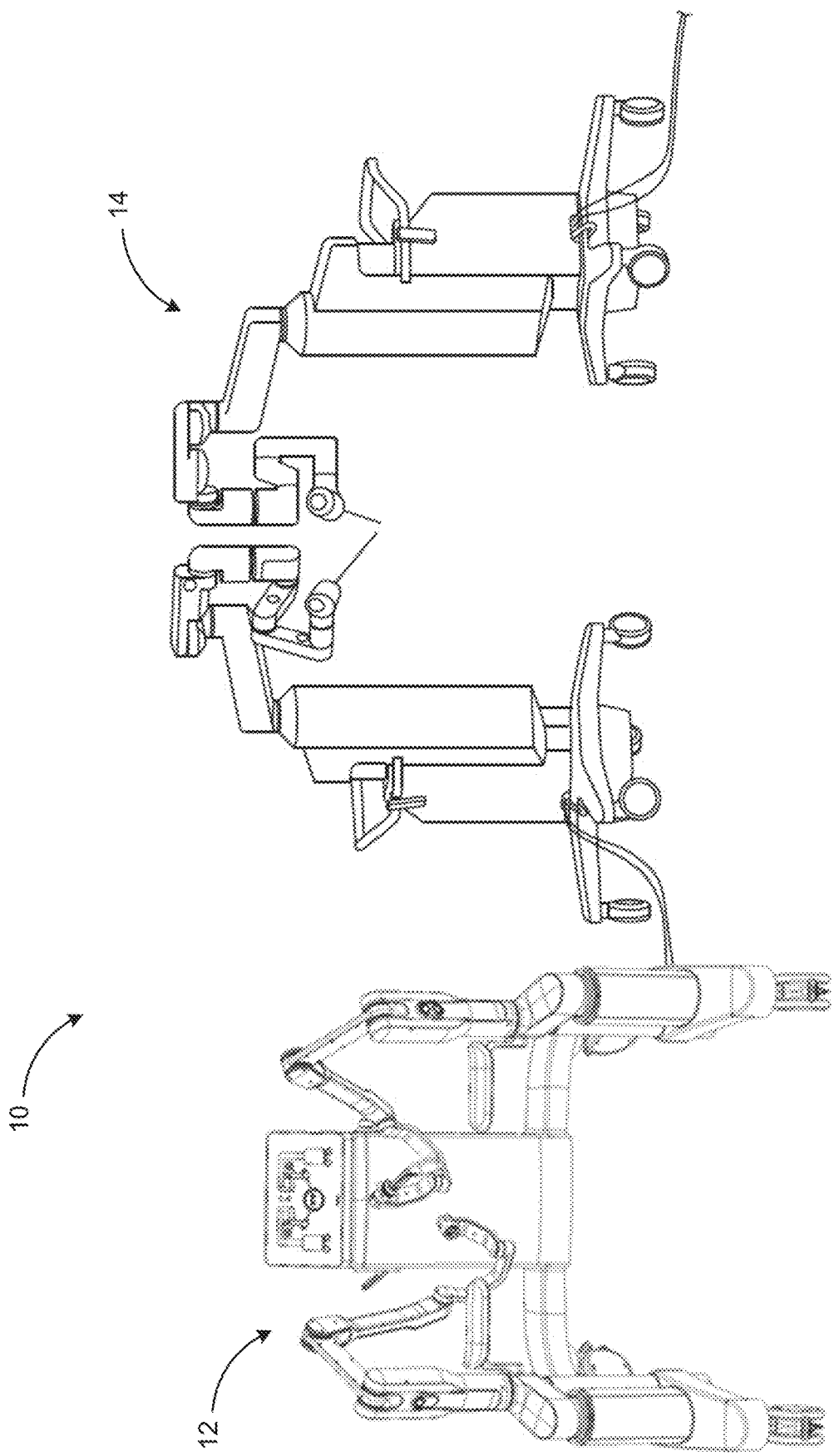
FIG. 1 illustrates an exemplary remotely actuated surgical robot system having robotic telemanipulators constructed in accordance with the principles of the present disclosure.

Referring now to FIG. 1, exemplary remotely actuated surgical robot system 10 having robotic telemanipulators is described. Surgical robot system 10 is a surgical platform and may be constructed as described in U.S. Pat. No. 10,413,374 to Chassot and/or International Patent Appl. Pub. No. WO 2020/141487 to Chassot, the entire contents of each of which are incorporated herein by reference. For example, as shown in FIG. 1, surgical robot system 10 includes surgeon console 12 electrically and operatively coupled to patient console 14 via, e.g., electrical cables. Surgeon console 12 includes a plurality of surgeon links interconnected by a plurality of surgeon joints, and patient console 14 includes a plurality of patient links interconnected by a plurality of patient joints.

A plurality of actuators, e.g., preferably motors, coupled to patient console 14 may apply translational macro-movements to an end-effector of patient console 14 responsive to movement applied at surgeon console 12 via a processor-driven control system, e.g., when surgical robot system 10 is in a macro-synchronization state. Additionally, a plurality of actuators, e.g., preferably motors, coupled to patient console 14 may apply micro-movements to an end-effector of patient console 14 responsive to movement applied at a handle of surgeon console 12 via the processor-driven control system, e.g., when surgical robot system 10 is in a micro-synchronization state. Accordingly, the patient links and joints of patient console 14 may move in a manner responsive to movement applied at the handle of surgeon console 12 such that the surgical instrument reproduces the movement applied at the handle of surgeon console 12.

Figure 2:
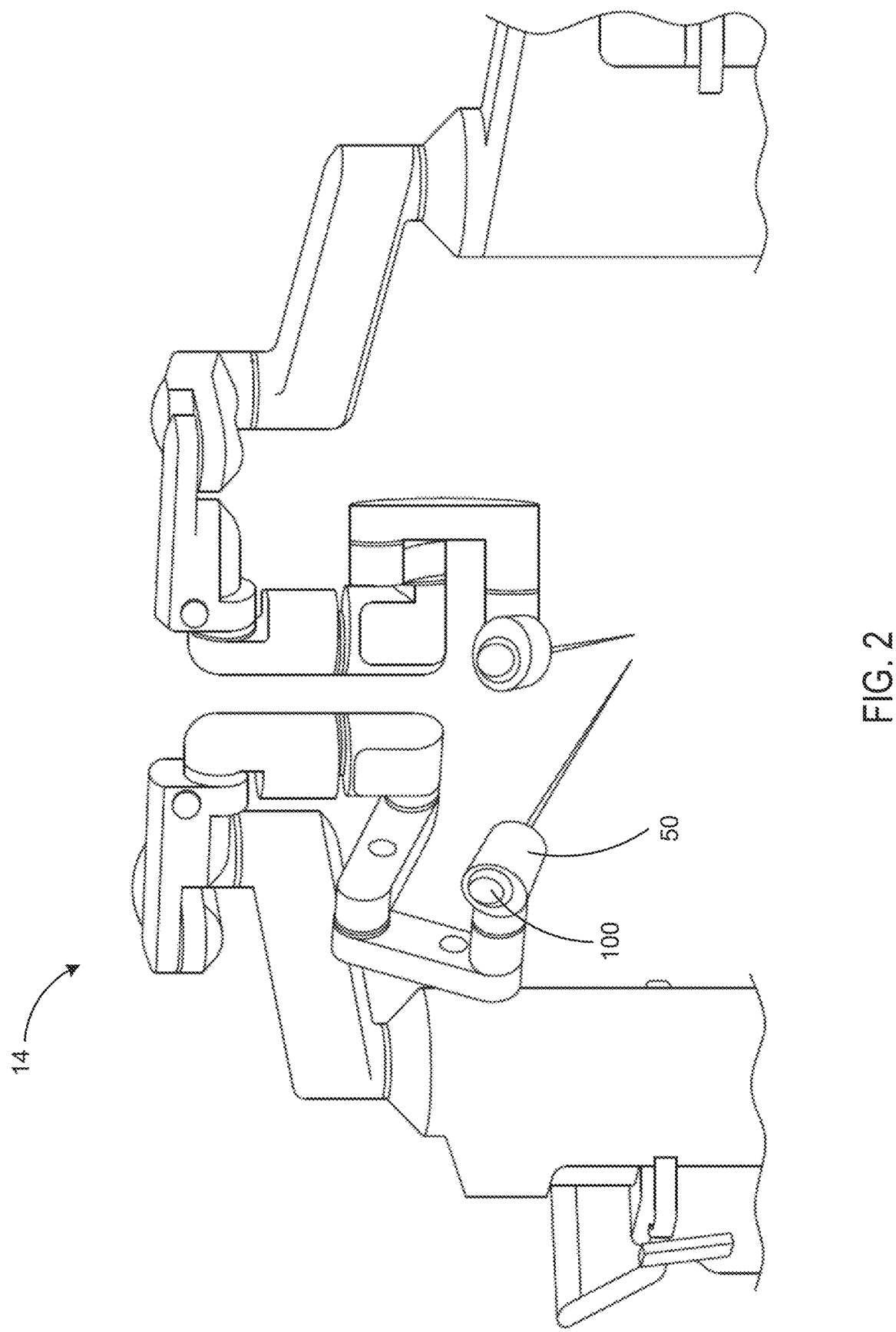
FIG. 2 illustrates an exemplary patient console of the system of FIG. 1 constructed in accordance with the principles of the present disclosure.

Referring now to FIG. 2, an exemplary patient console of surgical robot system 10 is provided. As shown in FIG. 2, a distal patient link of patient console 14 includes patient hub 50 for releasably engaging with a surgical instrument, e.g., surgical instrument 100, via the surgical instrument interface of the surgical instrument, as described in further detail below. Accordingly, patient console 14 may be actuated to cause surgical instrument 100 to reproduce the movement applied at the handle of surgeon console 12 via patient hub 50.

Figure 3A:
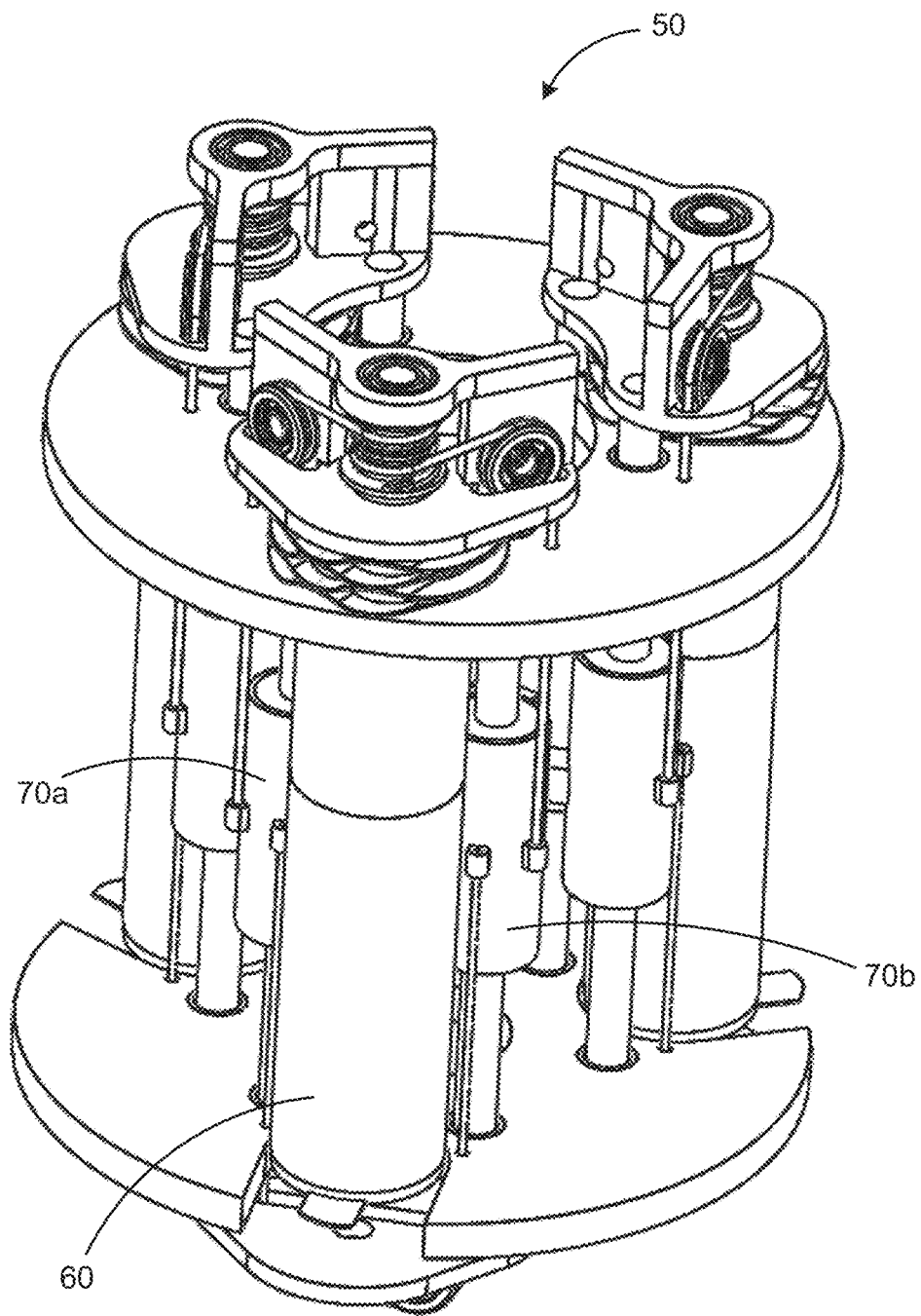
FIG. 3A illustrates an exemplary patient hub of the patient console of FIG. 2 constructed in accordance with the principles of the present disclosure.

Referring now to FIG. 3A, an exemplary patient hub of patient console 14 is provided. Patient hub 50 includes a translational instrument interface, which may be constructed as described in U.S. Pat. No. 11,058,503 to Chassot, the entire contents of which are incorporated herein by reference. For example, patient hub 50 may include one or more motors 60, each motor configured to actuate a pair of receptacles 70a, 70b. Each receptacle 70a, 70b includes an engager sized and shaped to engage with an actuator of the surgical instrument interface of surgical instrument 100, as described in further detail below. Accordingly, motor 60 may be actuated to cause receptacles 70a, 70b to translationally move in equal and opposite directions, e.g., a system of pulleys and cables or gears, which causes corresponding translational movement of the actuators of the surgical instrument interface of surgical instrument 100. Moreover, patient hub 50 includes a passageway extending therethrough, sized and shaped to receive surgical instrument 100 therethrough, such that the engagers of receptacles 70a, 70b engage with the actuators of the surgical instrument interface of surgical instrument 100.

Figure 3B:
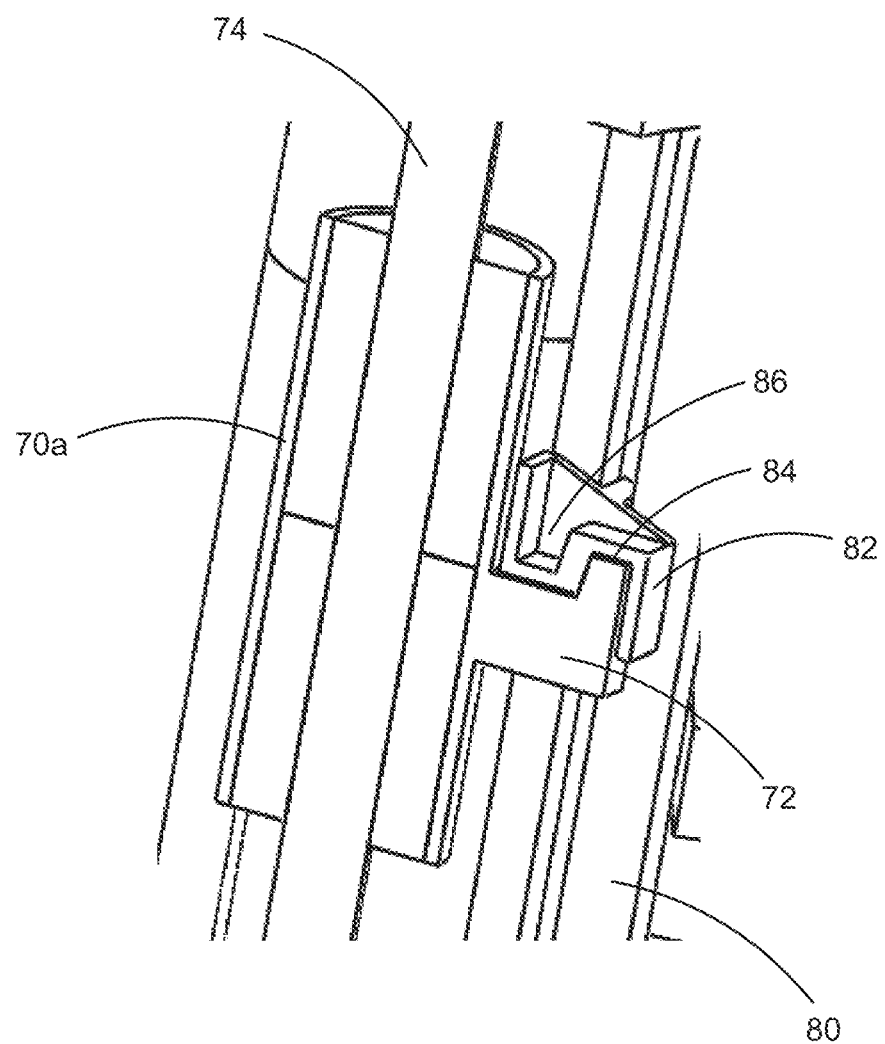
FIG. 3B illustrates an exemplary sterile shield coupled to the patient hub of FIG. 3A in accordance with the principles of the present disclosure.

Referring now to FIG. 3B, an exemplary sterile shield is provided. Sterile shield 80 may be constructed as described in U.S. Pat. No. 11,058,503 to Chassot, and may be positioned between the engagers of patient hub 50, e.g., engager 72 as shown in FIG. 3B, and the actuators of the surgical instrument interface of surgical instrument 100. Sterile shield 80 may include moveable slider 82 to provide a mechanical connection between receptacle 70a of patient hub 50 and the corresponding actuator of surgical instrument 100. As shown in FIG. 3B, sterile shield 80 has first portion 84 having a geometry corresponding to engager 72 such that first portion 84 may engage with engager 72, and second portion 86 having a geometry corresponding to the actuator of surgical instrument 100 such that second portion 86 may engage with the actuator of surgical instrument 100. Sterile shield 80 also may be integrated on a sterile sleeve to create a sterile barrier for the entire patient console 14.

Figure 4A:
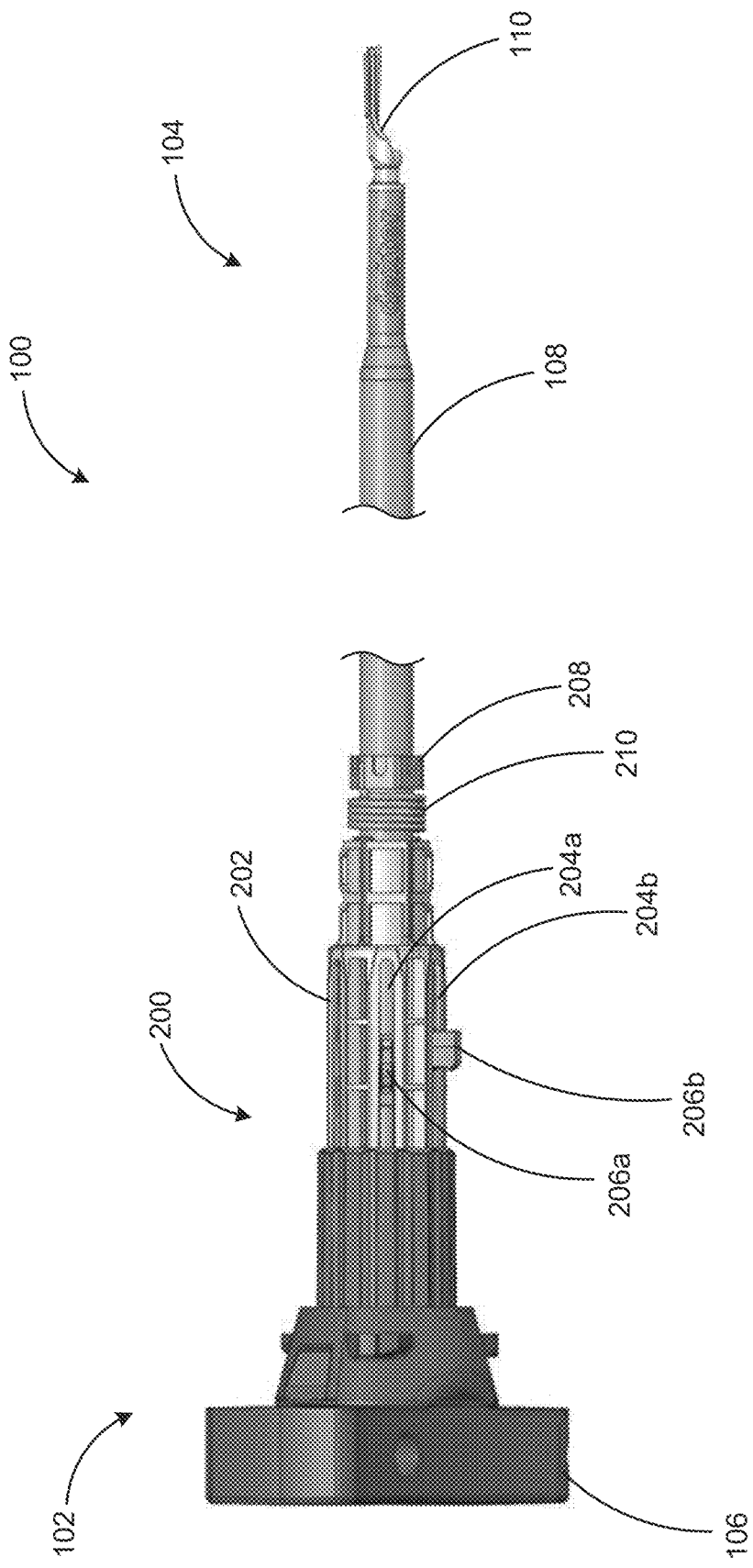
FIGS. 4A and 4B illustrate an exemplary surgical instrument constructed in accordance with the principles of the present disclosure.
Figure 4B:
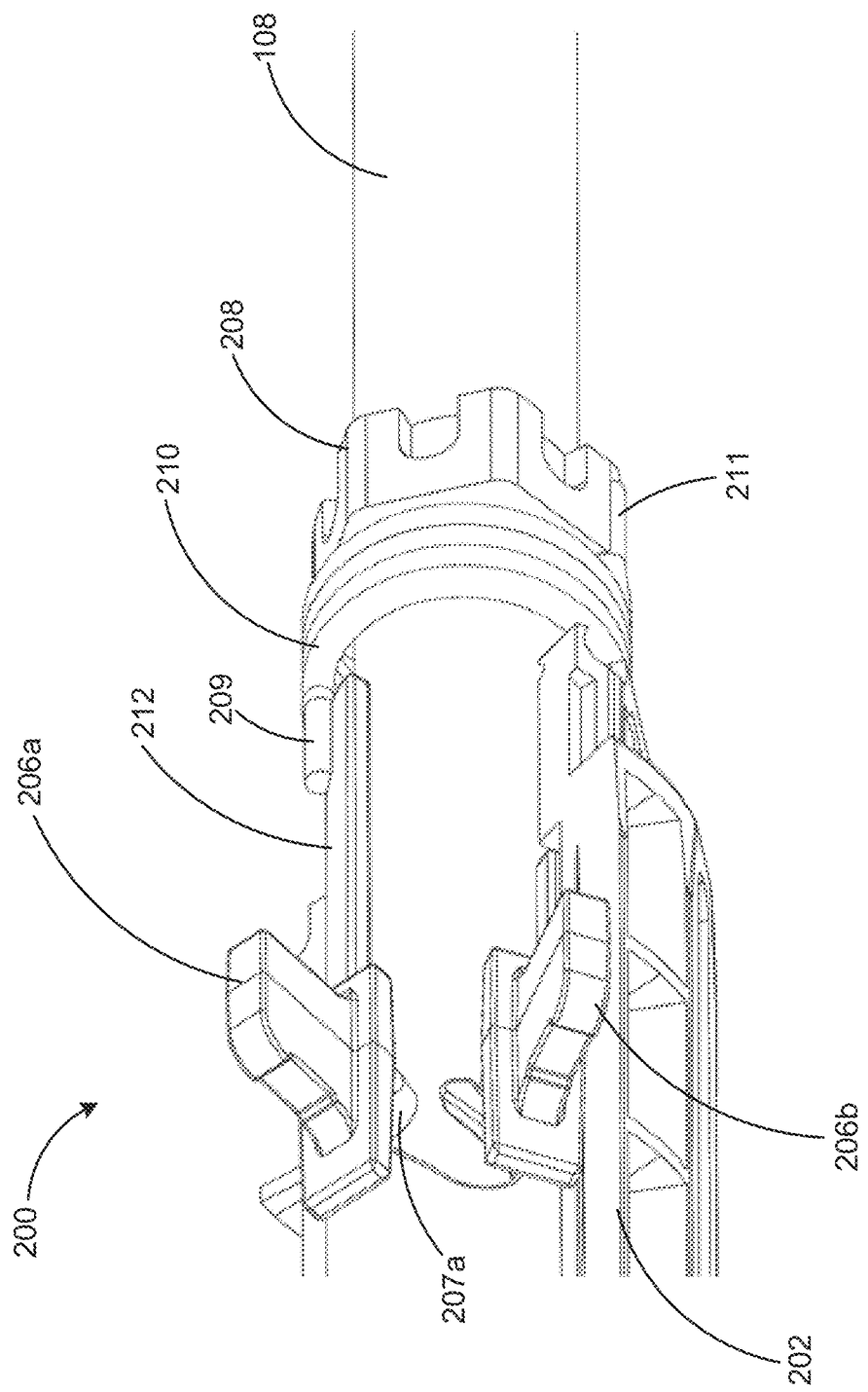

Referring now to FIGS. 4A and 4B, an exemplary surgical instrument is provided. Surgical instrument 100 may be interchangeable with various surgical platforms. For example, surgical instrument 100 may releasably engage with a surgical platform such as patient console 14 of surgical robot system 10, as described above. Additionally, surgical instrument 100 also may releasably engage with a surgical platform such a handheld surgical system, as described in further detail below. As shown in FIG. 4A, surgical instrument 100 may include surgical instrument interface 200 operatively coupled to end-effector 110 via instrument shaft 108. Accordingly, actuation of surgical instrument interface 200, e.g., via the engagers of patient hub 50, causes actuation of end-effector 110 via instrument shaft 108.

As shown in FIGS. 4A and 4B, surgical instrument interface 200 includes housing 202 having one or more longitudinal openings, and preferably, housing 202 has two longitudinal openings 204a, 204b. In addition, surgical instrument interface 200 includes barrel 212 rotatably disposed within and concentric with housing 202. Barrel 212 is coupled to instrument shaft 108. In some embodiments, barrel 212 may be coupled to instrument shaft 108 via torsion spring 210 and fixation ring 208. For example, proximal end 209 of spring 210 may be fixedly coupled to barrel 212, and distal end 211 of spring 210 may be fixedly coupled to fixation ring 208, which may be fixedly coupled to instrument shaft 108. Spring 210 may be pre-loaded with a predetermined torque by rotating fixation spring 208 relative to barrel 212, prior to fixing fixation ring 208 to instrument shaft 108. When the predetermined torque is achieved, fixation ring 208 may then be fixed to instrument shaft 108. The predetermined torque determines the maximum torque that may be transmitted between barrel 212 and instrument shaft 108 before torsional compression of spring 210, as described in further detail below.

Figure 6A:
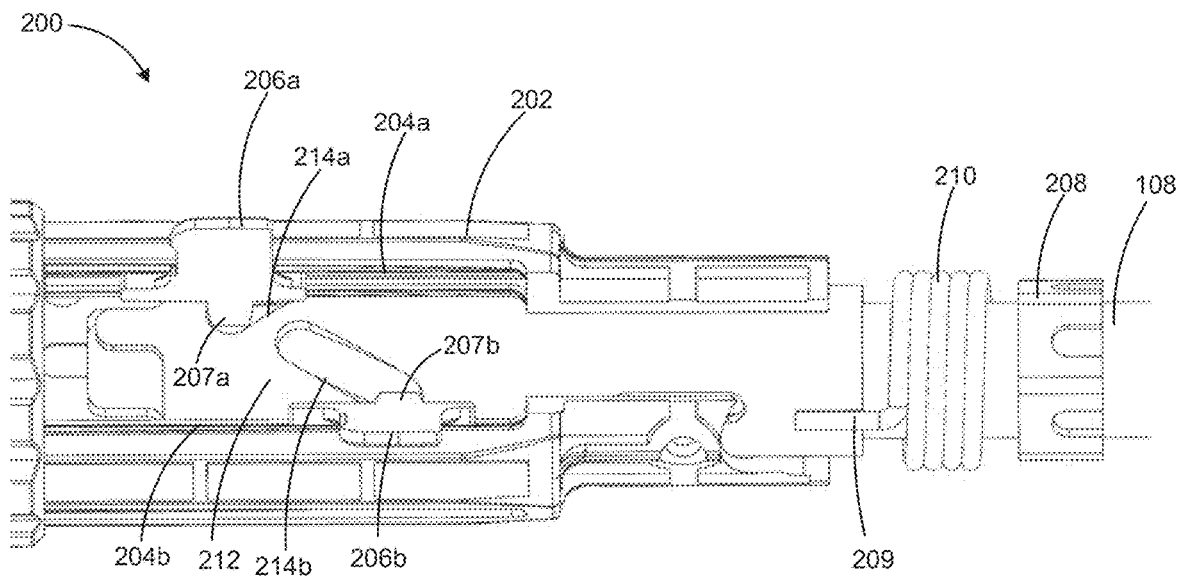
FIGS. 6A and 6B illustrate exemplary actuators of the surgical instrument of FIGS. 4A and 4B in accordance with the principles of the present disclosure.
Figure 6B:
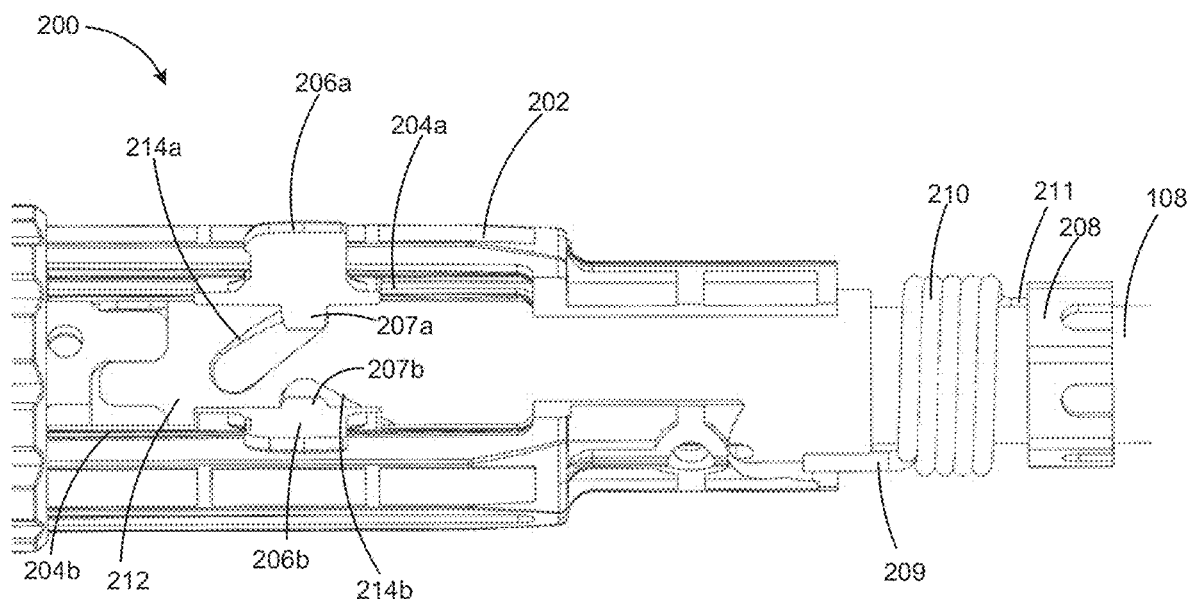

Moreover, as shown in FIGS. 4A and 4B, surgical instrument interface 200 includes one or more actuators, and preferably at least a pair of actuators 206a, 206b, slidably disposed within longitudinal openings 204a, 204b, respectively. Actuators 206a, 206b are sized and shaped to engage with the engagers of patient hub 50, e.g., via sterile shield 80. Accordingly, translational movement of receptacle 70a, and accordingly the engager attached thereto, in a first direction causes a corresponding translation movement of actuator 206a in the first direction within longitudinal opening 204a, and translational movement of receptacle 70b, and accordingly the engager attached thereto, in a second direction opposite to the first direction causes a corresponding translation movement of actuator 206b in the second direction within longitudinal opening 204b. In addition, each actuator 206a, 206b has engagement portion 207a, 207b (as shown in FIGS. 6A and 6B), respectively, extending radially inwardly toward the longitudinal axis of surgical instrument interface 200 through longitudinal openings 204a, 204b, respectively. Although FIGS. 4A and 4B show surgical instrument interface 200 having two actuators for actuating end-effector 110 in a degree-of-freedom, e.g., open/close, as will be understood by a person having ordinary skill in the art, in one embodiment, surgical instrument interface 200 may include only one actuator slidably disposed within a single longitudinal opening of housing 200 for actuating end-effector 110 in the open/close degree-of-freedom.

Engagement portions 207a, 207b slidably engage with a grooved opening of barrel 212, such that translation movement of actuator 206a, 206b causes barrel 212 to rotate along the grooved opening, as described in further detail below. Accordingly, when the torque generated by rotation of barrel 212 between barrel 212 and instrument shaft 108 is less than the predetermined torque of spring 210, rotation of barrel 212 causes instrument shaft 108 to rotate via spring 210. When the torque generated by rotation of barrel 212 between barrel 212 and instrument shaft 108 is greater than the predetermined torque of spring 210, rotation of barrel 212 causes spring 210 to compress torsionally, such that rotation torque of barrel 212 limits the torque transmitted to instrument shaft 108 to the torsion torque of spring 210, and accordingly, instrument shaft 108 may not rotate as barrel 212 rotates.

In addition, surgical instrument interface 200 may include identifier element 106 for permitting the control system of surgical robot system 10 to identify surgical instrument 100, as described in International Patent Appl. Pub. No. WO 2020/141487 to Chassot. For example, identifier element 106 may be an RFID token integrated with the instrument, which contains information on the kinematic configuration of surgical instrument 100.

Referring now to FIG. 5, an exemplary barrel is provided. Barrel 212 is rotatably disposed within and concentric with housing 202, and coupled to instrument shaft 108. For example, barrel 212 may be coupled to instrument shaft 108 via spring 110, as described above. As shown in FIG. 5, barrel 212 includes one or more grooved openings 214a, 214b extending circumferentially about at least a portion of barrel 212. Grooved openings 214a, 214b may be cut into barrel 212 and sized and shaped to slidably receive actuators 206a, 206b therethrough. Moreover, grooved openings 214a, 214b may be oppositely angled such that translational movement of actuators 206a, 206b within longitudinal openings 204a, 204b in equal and opposite directions causes barrel 212 to rotate along grooved openings 214a, 214b. In some embodiments, grooved openings 214a, 214b may be a single opening within barrel 212 having the oppositely angled geometries to permit equal and opposite translational movement of actuators 206a, 206b along the grooved opening. As further shown in FIG. 5, the proximal end of barrel 212 may include cam stop 218 for rotatably engaging with a cam ring fixed to instrument shaft 108 to facilitate rotation of instrument shaft 108, as described in further detail below. Cam stop 218 may include a plurality of fingers spatially and circumferentially disposed about the proximal end of barrel 212, and extending proximally from the proximal end of barrel 212.

Referring now to FIGS. 6A and 6B, exemplary actuators of the surgical instrument interface are provided. As shown in FIGS. 6A and 6B, engagement portions 207a, 207b of actuators 206a, 206b extend through longitudinal openings 204a, 204b of housing 202, respectively, and slidably engage with grooved openings 214a, 214b of barrel 212, respectively. FIG. 6A illustrates actuators 206a, 206b in a minimum position, such that actuator 206a is in its proximal-most position relative to longitudinal opening 204a and along grooved opening 214a, and actuator 206b is in its distal-most position relative to longitudinal opening 204b and along grooved opening 214b. In the minimum position, actuators 206a, 206b may be, e.g., 10 mm apart from each other, and spring 210 may be in its pre-loaded configuration. Moreover, as described in further detail below, in the minimum position, end-effector 110 may be in an open configuration.

Actuators 206a, 206b may be actuated, e.g., via the engagers of patient hub 50, such that actuator 206a translationally moves distally within longitudinal opening 204a and along grooved opening 214a, and actuator 206b translationally moves proximally within longitudinal opening 204b and along grooved opening 214b. FIG. 6B illustrates actuators 206a, 206b in a maximum position, such that actuator 206a is in its distal-most position relative to longitudinal opening 204a and along grooved opening 214a, and actuator 206b is in its proximal-most position relative to longitudinal opening 204b and along grooved opening 214b. Distal movement of actuator 206a within longitudinal opening 204a and proximal movement of actuator 206b within longitudinal opening 204b causes barrel 212 to rotate about the longitudinal axis of surgical instrument 100 due to engagement of engagement portions 207a, 207b with grooved openings 214a, 214b. For example, in the maximum position, barrel 212 may be rotated, e.g., 70 degrees from the minimum position. The amount of rotation of instrument shaft 108 due the rotation of barrel 212 may be dependent on the amount of torque generated between barrel 212 and instrument shaft 108, as described in further detail below. Moreover, the maximum amount of rotation of instrument shaft 108 may be dependent on the length and angle of grooved openings 214a, 214b of barrel 212. As shown in FIG. 6B, actuators 206a, 206b may be aligned in the maximum position. Moreover, as described in further detail below, in the maximum position, end-effector 110 may be in a closed configuration.

Figure 7A:
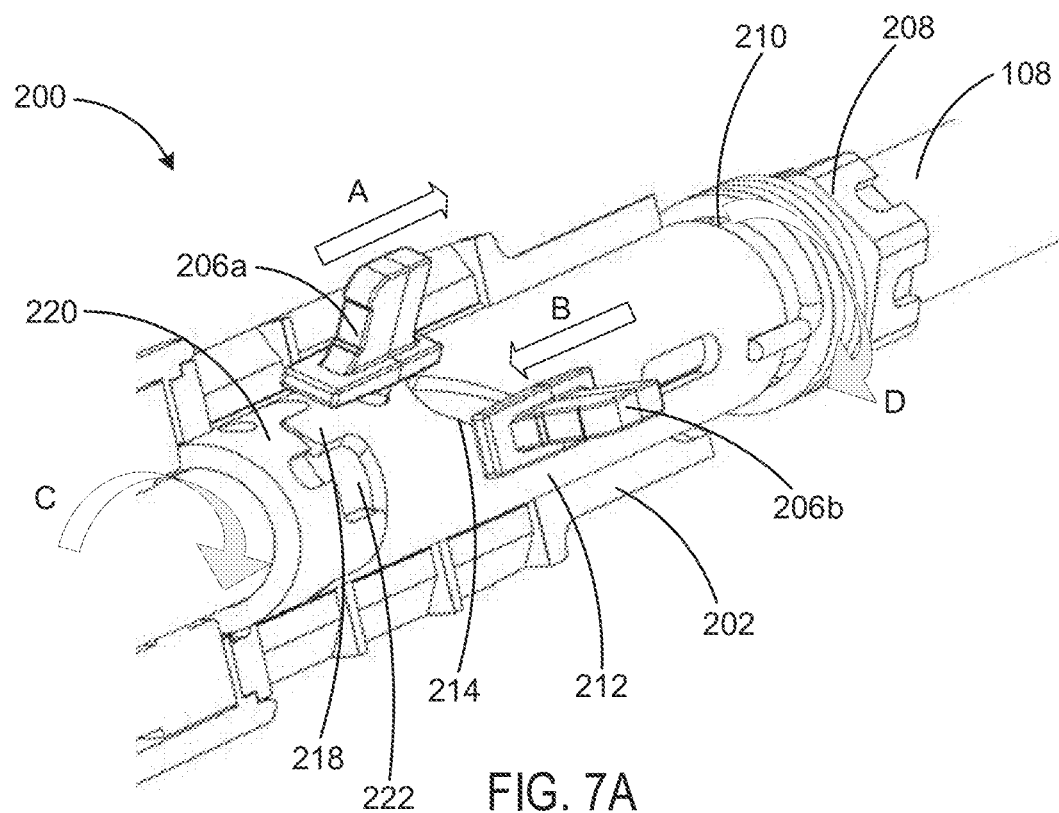
FIGS. 7A and 7B illustrate actuation of the surgical instrument of FIGS. 4A and 4B when the torque generated is less than the spring torque in accordance with the principles of the present disclosure.
Figure 7B:
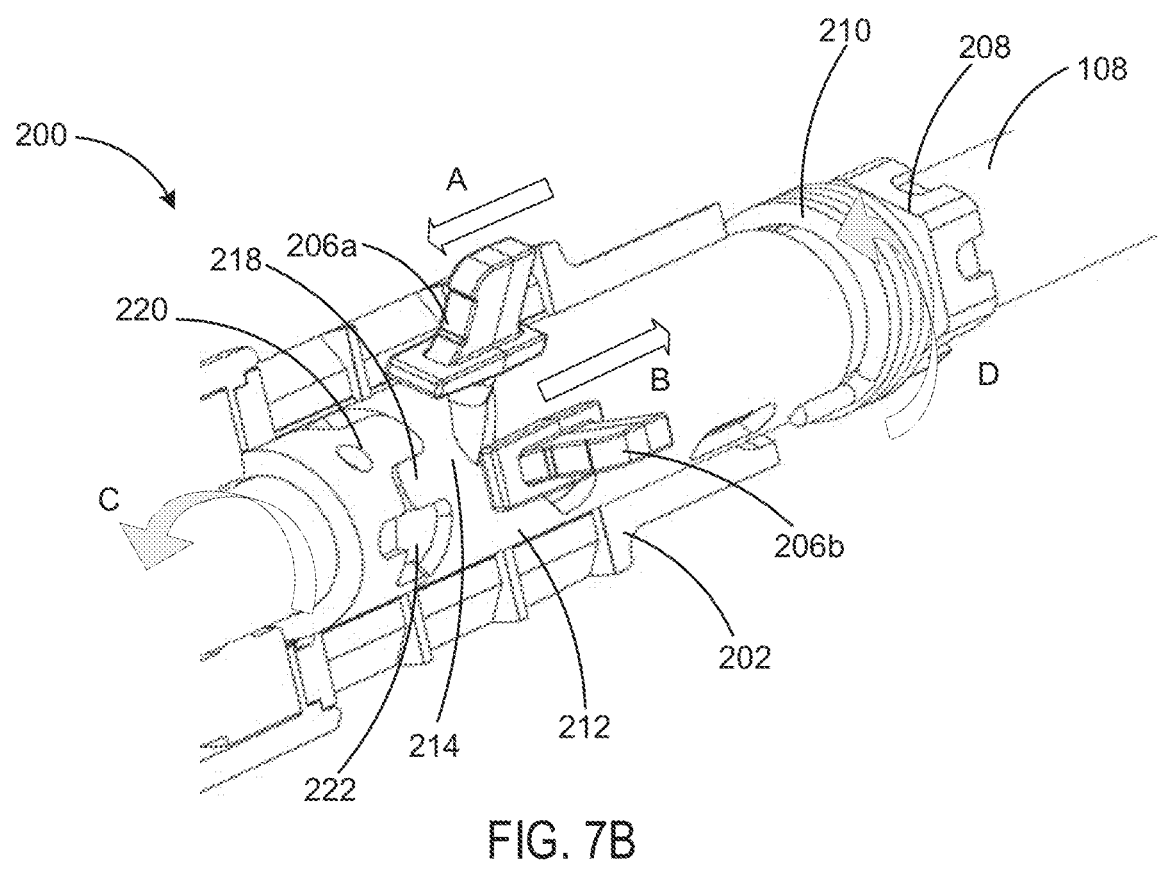

Referring now to FIGS. 7A and 7B, actuation of surgical instrument 100 when the torque generated between barrel 212 and instrument shaft 108 is less than the torque of spring 210 is described. FIG. 7A illustrates actuators 206a, 206b in the minimum position, e.g., actuator 206a is in its proximal-most position relative to grooved opening 214a and actuator 206b is in its distal-most position relative to grooved opening 214b. As shown in FIG. 7A, when going from the minimum position toward the maximum position, e.g., as actuator 206a moves distally in direction A and actuator 206b moves proximally in direction B, barrel 212 rotates in direction C due to engagement of actuators 206a, 206b with grooved openings 214a, 214b, respectively. In FIG. 7A, the actuation force of actuators 206a, 206b is such that the torque generated between barrel 212 and instrument shaft 108 is less than the predetermined torque of pre-loaded spring 210. Accordingly, rotation of barrel 212 in direction C causes rotation of instrument shaft 108 in direction D via spring 210 and fixation ring 208. As shown in FIG. 7A, cam ring 220 includes groove 222 sized and shaped to engage with cam stop 218, such that cam stop 218 may move circumferentially within groove 222. As both barrel 212 and instrument shaft 108 rotate due to actuation of actuators 206a, 206b when the torque generated between barrel 212 and instrument shaft 108 is less than the torque of spring 210, accordingly, both cam stop 218 of barrel 212 and cam ring 220 fixed to instrument shaft 108 also rotate.

As shown in FIG. 7B, when going from the maximum position toward the minimum position, e.g., as actuator 206a moves proximally in direction A and actuator 206b moves distally in direction B, barrel 212 rotates in direction C due to engagement of actuators 206a, 206b with grooved openings 214a, 214b, respectively. As barrel 212 rotates in direction C, cam stop 218 transmits torque to cam ring 220, e.g., within groove 222, to thereby cause cam ring 220, and accordingly instrument shaft 108, to rotate in direction D.

Figure 8A:
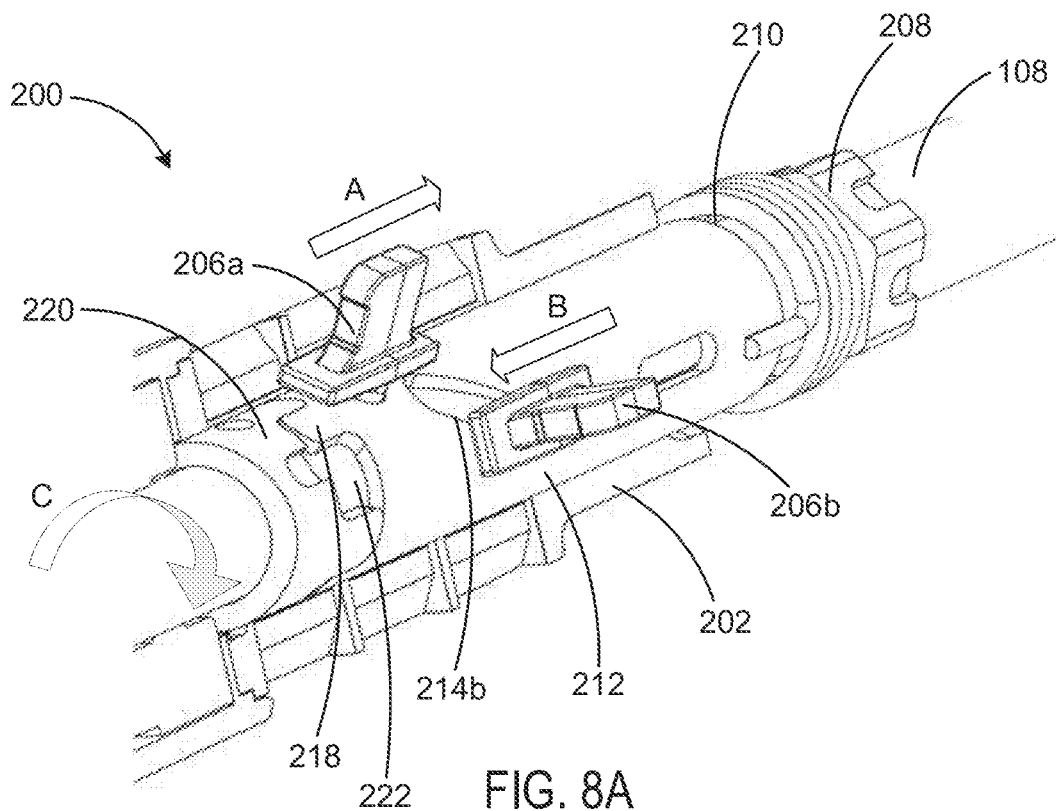
FIGS. 8A and 8B illustrate actuation of the surgical instrument of FIGS. 4A and 4B when the torque generated is greater than the spring torque in accordance with the principles of the present disclosure.
Figure 8B:
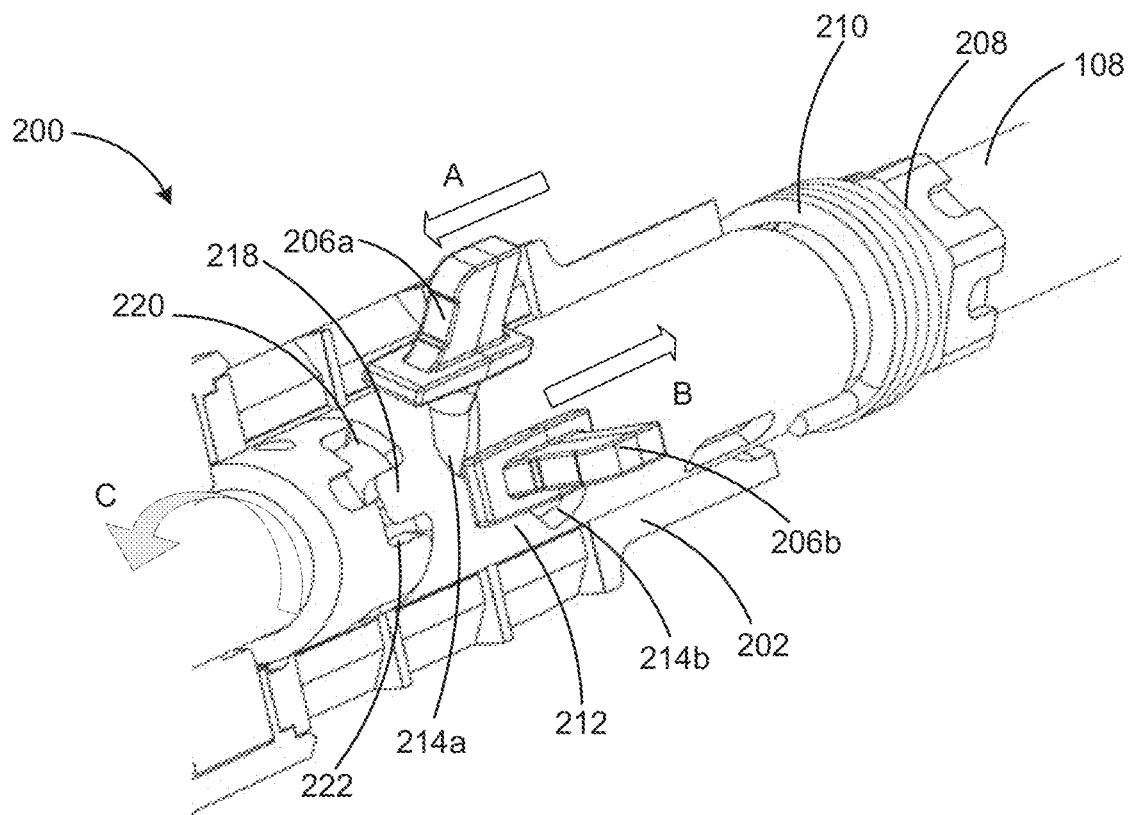

Referring now to FIGS. 8A and 8B, actuation of surgical instrument 100 when the torque generated between barrel 212 and instrument shaft 108 is greater than the torque of spring 210 is described. FIG. 8A illustrates actuators 206a, 206b in the minimum position, e.g., actuator 206a is in its proximal-most position relative to grooved opening 214a and actuator 206b is in its distal-most position relative to grooved opening 214b. As shown in FIG. 8A, when going from the minimum position toward the maximum position, e.g., as actuator 206a moves distally in direction A and actuator 206b moves proximally in direction B, barrel 212 rotates in direction C due to engagement of actuators 206a, 206b with grooved openings 214a, 214b, respectively. In FIG. 8A, the actuation force of actuators 206a, 206b is such that the torque generated between barrel 212 and instrument shaft 108 is greater than the predetermined torque of pre-loaded spring 210. Accordingly, spring 210 absorbs at least some of the torque generated between barrel 212 and instrument shaft 108, such that barrel 212 begins to rotate relative to instrument shaft 108 (instead of rotating synchronously with instrument shaft when the torque generated between barrel 212 and instrument shaft 108 is less than the predetermined torque of pre-loaded spring 210). Accordingly, spring 210 torsionally compresses, such that limited torque is transmitted from barrel 212 to instrument shaft 108 via spring 210. Accordingly, the maximum torque that the mechanism is able to transmit to instrument shaft 108 is equal to the sum of the preloaded predetermined torque of spring 210 and the additional rotation torque of the barrel multiplied by the stiffness of spring 210.

As shown in FIG. 8B, when actuators 206a, 206b are in the maximum position, and spring 210 is in a torsionally compressed configuration because the torque generated between barrel 212 and instrument shaft 108 due to actuation of actuators 206a, 206b is greater than the torque of spring 210, cam stop 218 is circumferentially moved relative to cam ring 220 within groove 218. This is because barrel 212 rotated, while rotation of instrument shaft 108 was limited. As further shown in FIG. 8B, when going from the maximum position toward the minimum position, e.g., as actuator 206a moves proximally in direction A and actuator 206b moves distally in direction B, barrel 212 rotates in direction C due to engagement of actuators 206a, 206b with grooved openings 214a, 214b, respectively. The torque generated from rotation of barrel 212 is first absorbed by spring 210, such that spring 210 torsionally releases its torque, until cam stop 218 engages with cam ring 220 within groove 222. Upon engagement of cam stop 218 with cam ring 220, further rotation of barrel 212 will cause torque to be transmitted from cam stop 218 to cam ring 220, to thereby cause corresponding rotation of instrument shaft 108.

Figure 9:
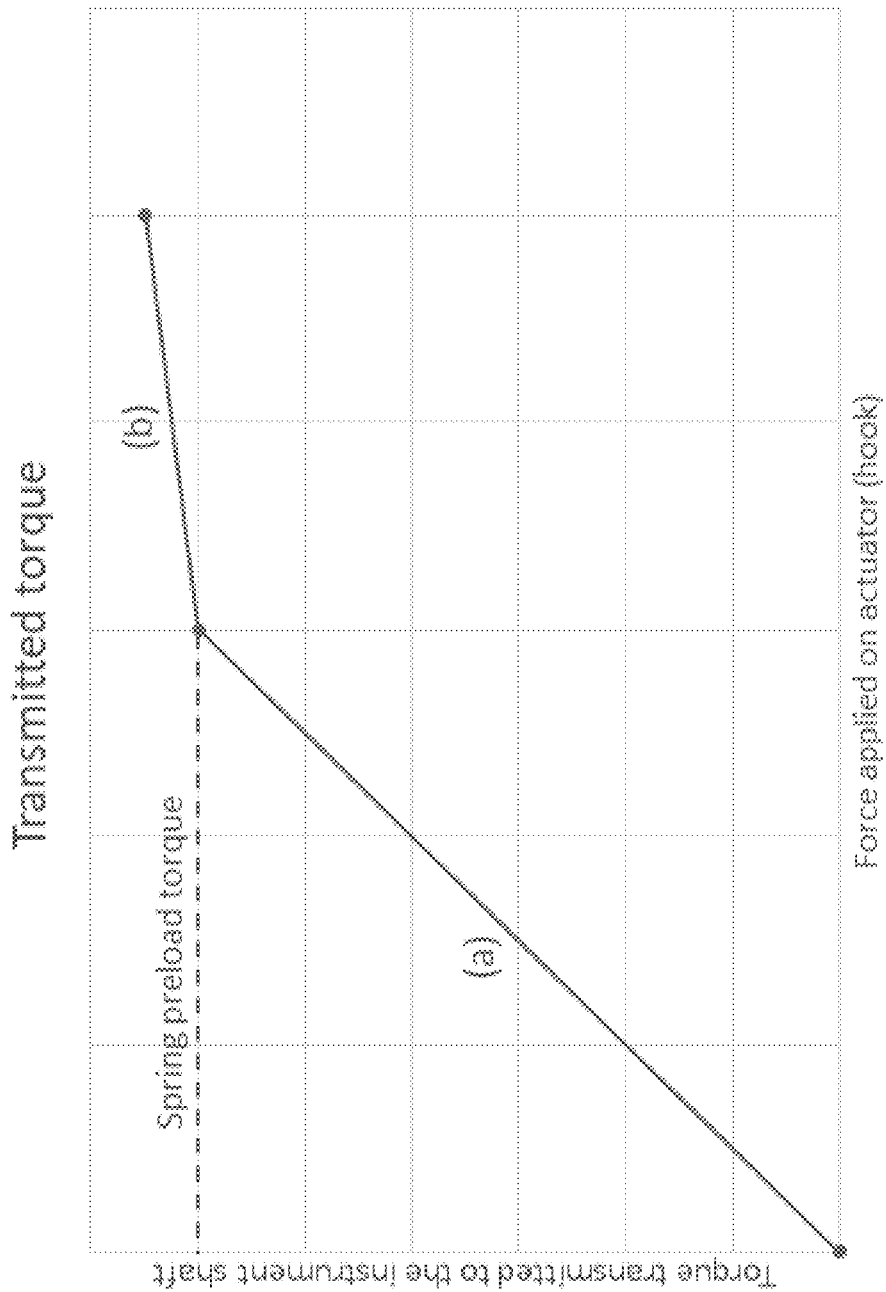
FIG. 9 is a graph illustrating torque transmission to the instrument shaft relative to the force applied to the actuators in accordance with the principles of the present disclosure.

FIG. 9 is a graph illustrating the transmission of torque from barrel 212 to instrument shaft 108 relative to the force applied to actuators 206a, 206b. As shown in FIG. 9, when the rotation barrel torque generated via force applied to actuators 206a, 206b is less than the predetermined torque of spring 210, the amount of torque transmitted from barrel 212 to instrument shaft 108 is equal to the rotation barrel torque, such that instrument shaft 108 rotates synchronously with barrel 212. Moreover, when the rotation barrel torque generated via force applied to actuators 206a, 206b is greater than the predetermined torque of spring 210, spring 210 limits the torque transmitted from barrel 212 to instrument shaft 108 as more force is applied to actuators 206a, 206b. The slope of the first portion (a) depends on the shape of the cam (e.g., grooved openings 214a, 214b) and on the yield of the transmission. The slope of the second portion (b) depends exclusively on the spring rate.

Figure 10A:
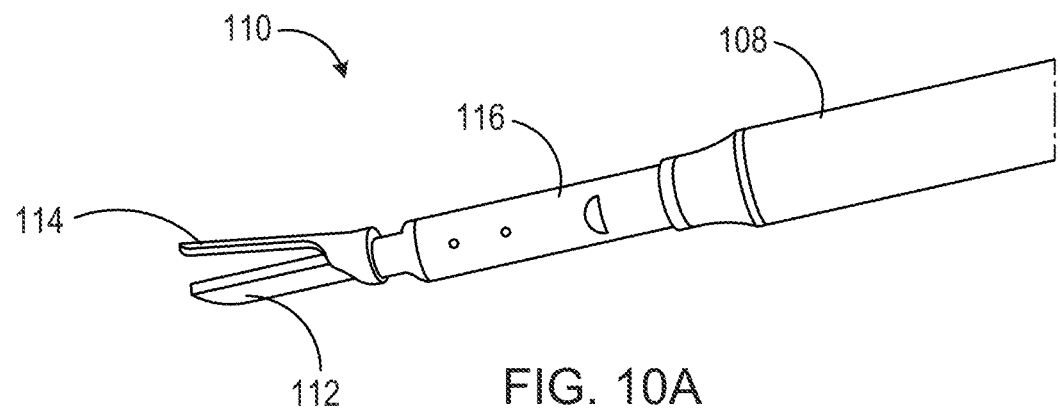
FIGS. 10A and 10B illustrate an exemplary end-effector of the surgical instrument of FIGS. 4A and 4B constructed in accordance with the principles of the present disclosure.
Figure 10B:
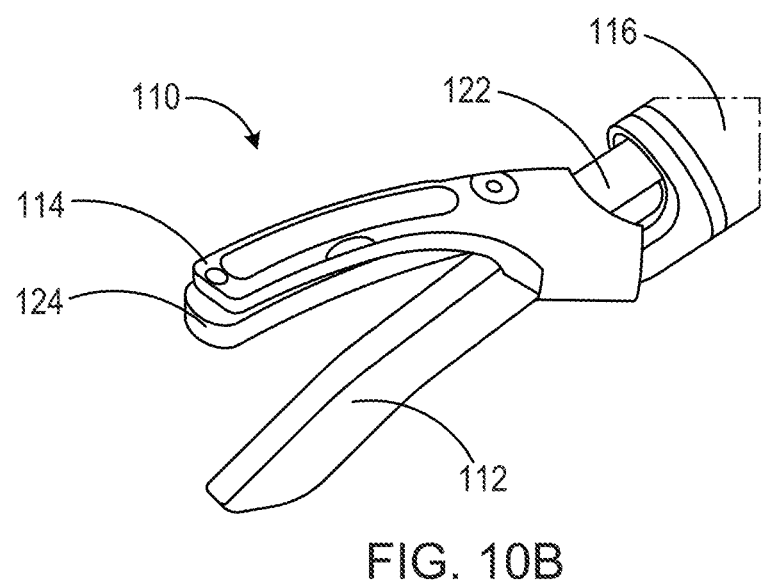

Referring now to FIGS. 10A and 10B, an exemplary end-effector is provided. End-effector 110 may be coupled to instrument shaft 108 via extension portion 116, which is fixed to instrument shaft 108. Alternatively, end-effector 110 may be directly coupled to instrument shaft 108 without extension portion 116. As shown in FIG. 10B, end-effector 110 may include a pair of jaws, e.g., jaws 112, 114. Jaw 112 may be fixedly coupled to rod 122, which remains stationary relative to housing 202 of surgical instrument interface 200 during operation of surgical instrument 100. Accordingly, rod 122 and jaw 112 may remain stationary as instrument shaft 108 rotates as described above.

Figure 10C:
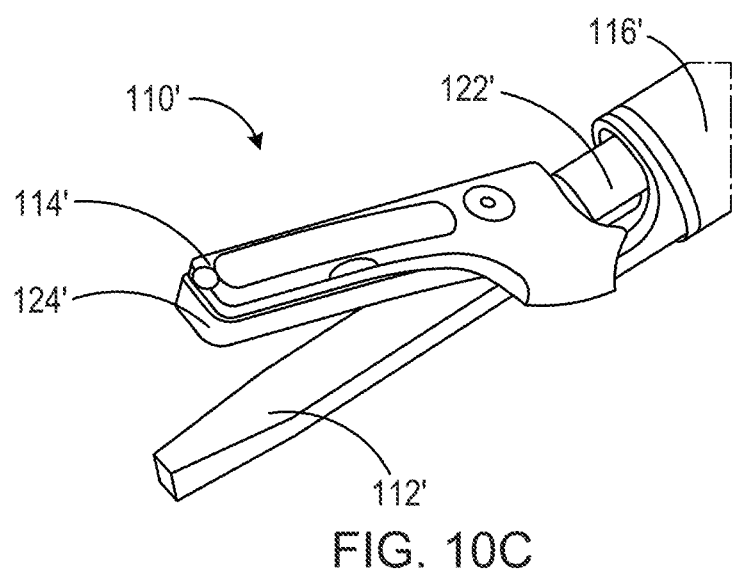
FIG. 10C illustrates an alternative exemplary end-effector of the surgical instrument constructed in accordance with the principles of the present disclosure.

Moreover, end-effector 110 may be configured to emit ultrasound energy to facilitate cutting and coagulation by the surgeon using surgical instrument 100. For example, end-effector 110 may be a Lotus ultrasonic scalpel (made available by BOWA-electronic GmbH & Co. KG, Gomaringen, Germany). Accordingly, ultrasonic energy may be transmitted via jaw 112 during actuation of surgical instrument 110. As shown in FIG. 10B, jaw 112 may have a narrow blade with focusing grooves for accurate dissection. Moreover, jaw 114 may include electrically insulated portion 124, which contacts jaw 112 in the closed position, thereby facilitating cutting and coagulation by end-effector 110. Alternatively, as shown in FIG. 10C, jaw 112' may have a larger contact surface, thereby providing a stronger hemostatic effect.

Referring now to FIGS. 11A and 11B, actuation of the end-effector of surgical instrument 100 is described. End-effector 110 may be operatively coupled to extension portion 116 of instrument shaft 108 via a cam mechanism, as described in U.S. 2005/0216045 to Young, the entire contents of which are incorporated herein by reference. Specifically, as shown in FIG. 11A, extension portion 116 may include cam 118, and jaw 114 may include follower 120 having a geometry sized and shaped to engage with cam 118. Jaw 112 is omitted for brevity. As instrument shaft 108, and accordingly extension portion 116 and cam 118 rotates, jaw 114 transitions between an open configuration in the minimum position and a closed configuration in the maximum position due to the engagement of cam 118 and follower 120. For example, as shown in FIG. 11A, in the minimum position, jaw 114 is in its open configuration.

As shown in FIG. 11B, when instrument shaft 108, and accordingly extension portion 116 and cam 118 rotates from the minimum position to the maximum position, the rotation of cam 118 causes jaw 114 to transition from the open configuration to the closed configuration as follower 120 pivots about cam 118. Accordingly, cables are not required to be routed through instrument shaft 108 of surgical instrument 100 in order to actuate end-effector 110. Jaws 112 and 114 may dissect tissue as jaw 114 transitions from the open configuration to the closed configuration. Surgical instrument 100 further may be actuated to emit ultrasonic energy to facilitate cutting and coagulation of the tissue during operation of surgical instrument 100.

Figure 12:
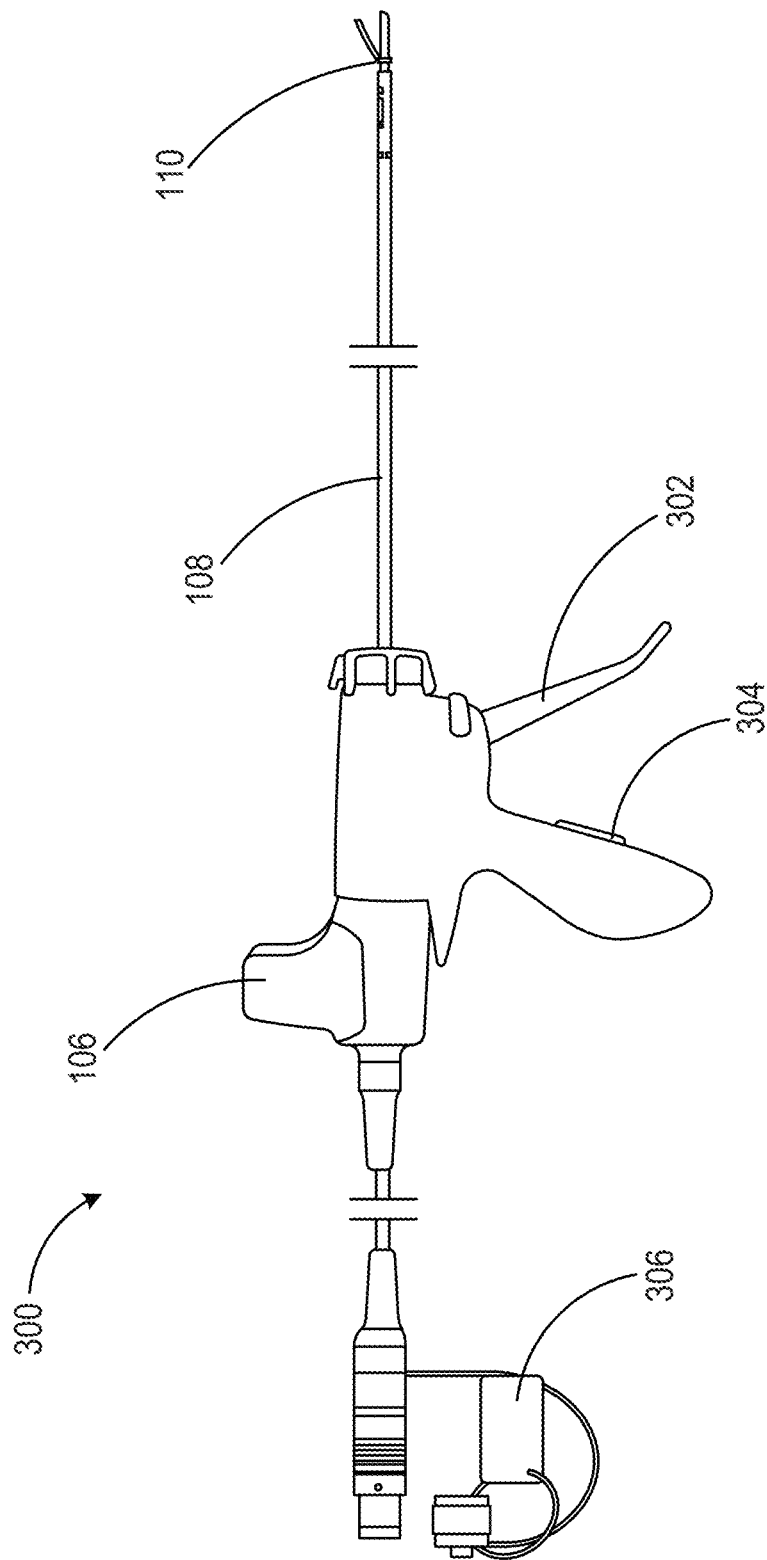
FIG. 12 illustrates the surgical instrument of FIGS. 4A and 4B coupled to a handheld surgical system in accordance with the principles of the present disclosure.

Referring now to FIG. 12, surgical instrument may be releasably engaged with an exemplary handheld surgical system. Handheld surgical system 300 may be a Lotus system (made available by BOWA-electronic Gmbh & Co. KG, Gomaringen, Germany). As shown in FIG. 12, system 300 may include trigger 302, power actuator 304, and transducer 306. Trigger 302 may be actuated by the surgeon to cause translational movement of engagers of system 300, which are engaged with actuators 206a, 206b when surgical instrument 100 is coupled to system 300. Accordingly, translational movement of the engagers of system 300 will cause translational movement of actuators 206a, 206b, which will cause rotation of instrument shaft 108 if the torque generated between barrel 212 and instrument shaft 108 is less than the predetermined torque of spring 210, or will not cause rotation of instrument shaft due to compression of spring 210 if the torque generated between barrel 212 and instrument shaft 108 is greater than the predetermined torque of spring 210, as described above. In addition, power actuator 304 of system 300 may be actuated to cause end-effector 110 to emit ultrasonic energy during operation of system 300. Transducer 306 provides power for actuating end-effector 110 via power actuator 304, and may be releasably coupled to system 300. Moreover, transducer 306 may be reusable.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A surgical instrument interface operatively coupled to an instrument shaft having an end-effector, the surgical instrument interface comprising:
   a housing comprising a longitudinal opening;
   a barrel rotatably disposed within the housing, the barrel comprising a grooved opening extending circumferentially along at least a portion of the barrel;
   a spring having a proximal end coupled to the barrel and a distal end coupled to the instrument shaft, the spring configured to be pre-loaded with a predetermined torque; and
   an actuator slidably disposed within the longitudinal opening and engaged with the grooved opening, such that translational movement of the actuator along the longitudinal opening causes the barrel to rotate along the grooved opening to thereby rotate the instrument shaft,
   wherein translational movement of the actuator along the longitudinal opening causes the barrel to rotate along the grooved opening to thereby rotate the instrument shaft via the spring.

2. The surgical instrument interface of claim 1, wherein rotation of the barrel causes the instrument shaft to rotate when a torque generated by rotation of the barrel between the barrel and the instrument shaft is less than the predetermined torque of the spring.

3. The surgical instrument interface of claim 2, wherein, when the torque generated by rotation of the barrel between the barrel and the instrument shaft is less than the predetermined torque of the spring, the spring is configured to transmit the torque to the instrument shaft to rotate the instrument shaft in a first direction.

4. The surgical instrument interface of claim 3, wherein the barrel comprises a cam stop configured to engage with a cam ring fixed to the instrument shaft, and wherein, when the torque generated by rotation of the barrel between the barrel and the instrument shaft is less than the predetermined torque of the spring, the cam stop is configured to transmit the torque to the instrument shaft via the cam ring to rotate the instrument shaft in a second direction opposite to the first direction.

5. The surgical instrument interface of claim 4, wherein the cam stop extends proximally from a proximal end of the barrel, and wherein the cam ring comprises a distal opening sized and shaped to receive the cam stop and to permit the cam stop to circumferentially move within the distal opening.

6. The surgical instrument interface of claim 1, wherein, when a torque generated by rotation of the barrel between the barrel and the instrument shaft is greater than the predetermined torque of the spring, rotation of the barrel in a first direction causes the spring to compress torsionally such that rotation torque of the barrel in the first direction limits the torque transmitted to the instrument shaft to the torsion torque of the spring.

7. The surgical instrument interface of claim 6, wherein, rotation of the barrel in a second direction opposite to the first direction causes the spring to absorb movement of the barrel until the barrel is able to transmit torque to the instrument shaft.

8. The surgical instrument interface of claim 1, wherein the distal end of the spring is coupled to the instrument shaft via a fixation ring, the fixation ring configured to be actuated to pre-load the spring with the predetermined torque.

* * * * *